(12) United States Patent
Madabhushi et al.

(10) Patent No.: US 11,983,868 B2
(45) Date of Patent: May 14, 2024

(54) PREDICTING NEO-ADJUVANT CHEMOTHERAPY RESPONSE FROM PRE-TREATMENT BREAST MAGNETIC RESONANCE IMAGING USING ARTIFICIAL INTELLIGENCE AND HER2 STATUS

(71) Applicant: Case Western Reserve University, Cleveland, OH (US)

(72) Inventors: Anant Madabhushi, Shaker Heights, OH (US); Nathaniel Braman, Cleveland, OH (US); Kavya Ravichandran, Westlake, OH (US); Andrew Janowczyk, East Meadow, NY (US)

(73) Assignee: Case Western Reserve University, Cleveland, OH (US)

( * ) Notice: Subject to any disclaimer, the term of this patent is extended or adjusted under 35 U.S.C. 154(b) by 1423 days.

(21) Appl. No.: 16/280,322

(22) Filed: Feb. 20, 2019

(65) Prior Publication Data
US 2019/0259157 A1 Aug. 22, 2019

Related U.S. Application Data

(60) Provisional application No. 62/633,311, filed on Feb. 21, 2018.

(51) Int. Cl.
*G06T 7/00* (2017.01)
*G06V 10/44* (2022.01)
(Continued)

(52) U.S. Cl.
CPC .......... *G06T 7/0012* (2013.01); *G06T 7/0014* (2013.01); *G06V 10/454* (2022.01);
(Continued)

(58) Field of Classification Search
CPC ........ G06T 7/0014; G16B 5/00; G16B 40/00; G16B 50/00
(Continued)

(56) References Cited

U.S. PATENT DOCUMENTS

2020/0364855 A1* 11/2020 Ha ....................... G06T 3/4046

OTHER PUBLICATIONS

DeGrandchamp et al, "Predicting response before initiation of neoadjuvant chemotherapy in breast cancer using new methods for the analysis of dynamic contrast enhanced MRI (DCE MRI) data," Proc. SPIE 9788, Medical Imaging 2016: Biomedical Applications in Molecular, Structural, and Functional Imaging (Year: 2016).*

(Continued)

*Primary Examiner* — Russell S Negin
*Assistant Examiner* — Guozhen Liu
(74) *Attorney, Agent, or Firm* — Eschweiler & Potashnik, LLC

(57) ABSTRACT

Embodiments predict response to neoadjuvant chemotherapy (NAC) in breast cancer (BCa) from pre-treatment dynamic contrast enhanced magnetic resonance imaging (DCE-MRI). Embodiments compute, using a machine learning (ML) classifier, a first probability of response based on a set of radiomic features extracted from a tumoral region represented in a pre-treatment DCE-MRI image of a region of tissue (ROT) demonstrating BCa; extract patches from the tumoral region; provide the patches to a convolutional neural network (CNN); receive, from the CNN, a pixel-level localized patch probability of response; compute a second probability of response based on the pixel-level localized patch probability; compute a combined ML probability from the first and second probabilities; compute a final probability of response based on the combined ML probability and clinical information associated with the ROT; classify the ROT as a responder or non-responder based on the final probability of response; and display the classification.

20 Claims, 12 Drawing Sheets

(51) Int. Cl.
  G06V 10/764 (2022.01)
  G06V 10/80 (2022.01)
  G06V 10/82 (2022.01)
  G16B 5/00 (2019.01)
  G16B 40/00 (2019.01)
  G16B 50/00 (2019.01)
(52) U.S. Cl.
  CPC .......... *G06V 10/764* (2022.01); *G06V 10/809* (2022.01); *G06V 10/82* (2022.01); *G16B 5/00* (2019.02); *G16B 40/00* (2019.02); *G16B 50/00* (2019.02)
(58) Field of Classification Search
  USPC .......................................................... 702/19
  See application file for complete search history.

(56) References Cited

OTHER PUBLICATIONS

Antropova et al: "Performance comparison of deep learning and segmentation-based radiomic methods in the task of distinguishing benign and malignant breast lesions on DCE-MRI," Proc. SPIE 10134, Medical Imaging 2017: Computer-Aided Diagnosis, 101341G (Mar. 3, 2017); (Year: 2017).*

Marrone et al: "An Investigation of Deep Learning for Lesions Malignancy Classification in Breast DCE-MRI", Image Analysis and Processing—ICIAP 2017, 19th International Conference, Catania, Italy, Sep. 11-15, 2017 (Year: 2017).*

Prasanna, P., Tiwari, P. & Madabhushi, A. "Co-occurrence of Local Anisotropic Gradient Orientations (CoLIAGe): A new radiomics descriptor". Sci Rep 6, 37241 (2016). (Year: 2016).*

Nedevschi et al: "Colorectal cancer recognition from ultrasound images, using complex textural microstructure cooccurrence matrices, based on Laws' features," 2015 38th International Conference on Telecommunications and Signal Processing (TSP), 2015, pp. 458-462 (Year: 2015).*

Roberta Fusco, Mario Sansone, Salvatore Filice, Guglielmo Carone, Daniela Maria Amato, Carlo Sansone, Antonella Petrillo: "Pattern Recognition Approaches for Breast Cancer DCE-MRI Classification: A Systematic Review", J. Med. Biol. Eng. (2016) 36: 449-459 (Year: 2016).*

Reza Rasti, Mohammad Teshnehlab, Son Lam Phung: "Breast cancer diagnosis in DCE-MRI using mixture ensemble of convolutional neural networks", Pattern Recognition 72 (2017) 381-390 (Year: 2017).*

David M.J. Tax, Martijn van Breukelen, Robert P.W. Duin, Josef Kittler: Combining multiple classi"ers by averaging or by multiplying? Pattern Recognition 33 (2000) 1475}1485 (Year: 2000).*

Keiller Nogueira, Waner O. Miranda, Jefersson A. dos Santos: ("Improving Spatial Feature Representation from Aerial Scenes by Using Convolutional Networks," 2015 28th SIBGRAPI Conference on Graphics, Patterns and Images, 2015). (Year: 2015).*

Braman : "Intratumoral and peritumoral radiomics for the pretreatment prediction of pathological complete response to neoadjuvant chemotherapy based on breast DCE-MRI", Breast Cancer Research (2017) 19:57 (Year: 2017).*

Gillies, Robert J., Paul E. Kinahan, and Hedvig Hricak. "Radiomics: images are more than pictures, they are data." Radiology 278.2 (2016): 563-577. (Year: 2016).*

Fan, Ming, et al. "Radiomic analysis of DCE-MRI for prediction of response to neoadjuvant chemotherapy in breast cancer patients." European journal of radiology 94 (2017): 140-147. (Year: 2017).*

* cited by examiner

PREDICTING NEO-ADJUVANT CHEMOTHERAPY RESPONSE FROM PRE-TREATMENT BREAST MAGNETIC RESONANCE IMAGING USING ARTIFICIAL INTELLIGENCE AND HER2 STATUS

CROSS REFERENCE TO RELATED APPLICATIONS

This application claims the benefit of U.S. Provisional Application 62/633,311 filed Feb. 21, 2018, which is incorporated by reference herein in its entirety.

FEDERAL FUNDING NOTICE

This invention was made with government support under CA179327, CA195152, CA199374, CA202752, CA208236, CA221383, DK098503, EB007509, and RR012463 awarded by the National Institutes of Health; and W81XWH-13-1-0418, W81XWH-14-1-0323, and W81XWH-16-1-0329 awarded by the Department of Defense. The government has certain rights in the invention.

BACKGROUND

Neo-adjuvant chemotherapy (NAC) is routinely used to treat breast tumors before surgery to reduce tumor size and improve outcome. Many breast cancer (BCa) patients who receive NAC will ultimately fail to achieve pathological complete response (pCR). pCR, which may include the absence of residual invasive disease in the breast or lymph nodes, is used a metric for the efficacy of NAC. However, no current clinical or imaging metrics effectively predict before treatment which NAC recipients will achieve pCR. Clinical assessment of baseline, pre-treatment dynamic contrast-enhanced magnetic resonance imaging (DCE-MRI) is not predictive of pCR. Thus, a pre-treatment clinical marker of pCR would be advantageous for guiding NAC without requiring a potentially ineffective initial treatment period.

BRIEF DESCRIPTION OF THE DRAWINGS

The accompanying drawings, which are incorporated in and constitute a part of the specification, illustrate various example operations, apparatus, methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that, in some examples, one element may be designed as multiple elements or that multiple elements may be designed as one element. In some examples, an element shown as an internal component of another element may be implemented as an external component and vice versa. Furthermore, elements may not be drawn to scale.

DETAILED DESCRIPTION

Many BCa patients who receive NAC will ultimately fail to achieve pCR. Assessment of baseline, pre-treatment DCE-MRI imagery is not predictive clinically of pCR. Patients who achieve pCR have better survival and are more likely to benefit from breast-conserving surgery, sparing them a full mastectomy. For the 10-50% of patients who will not respond to NAC, the lack of pre-treatment predictors of response necessitates a window of ineffective treatment that introduces unnecessary suffering and cost, delays effective treatment, and may increase risk of progression and metastasis. Therefore, a pre-treatment clinical marker of pCR would be advantageous for guiding NAC without requiring a potentially ineffective initial treatment period.

Embodiments predict response to NAC in BCa patients from pre-treatment imagery using a non-invasive, machine learning approach that includes deep learning, including pattern recognition using neural networks, radiomics, including computer-extracted quantitative image features, and clinical variables. Embodiments employ a combined machine learning (ML) model. The combined ML model includes providing pre-treatment DCE-MRI imagery of a region of tissue demonstrating cancerous pathology to a deep learning classifier and to a machine learning radiomic feature-based classifier. The machine learning radiomic feature-based classifier produces a first probability of response based on radiomic features extracted from the pre-treatment DCE-MRI imagery. The deep learning classifier produces a second probability of response based on patches extracted from the same pre-treatment DCE-MRI imagery. Embodiments generate a combined ML score based on the first probability and the second probability. Embodiments combine the combined ML score with clinical variables associated with the region of tissue using a multinomial regression model to generate a final probability of response. Embodiments may also train the deep learning classifier or the machine learning radiomic feature-based classifier to distinguish tissue, including tumors, which will experience response, from tissue, including tumors, that will not experience response. Embodiments may further classify the region of tissue (e.g., the tumor) as a responder or non-responder based, at least in part, on the final probability. Embodiments may classify the patient of which the imagery was acquired as a responder or non-responder based, at least in part, on the final probability or the classification. Embodiments may further generate a personalized cancer treatment plan based on the classification or the final probability.

Figure 1:
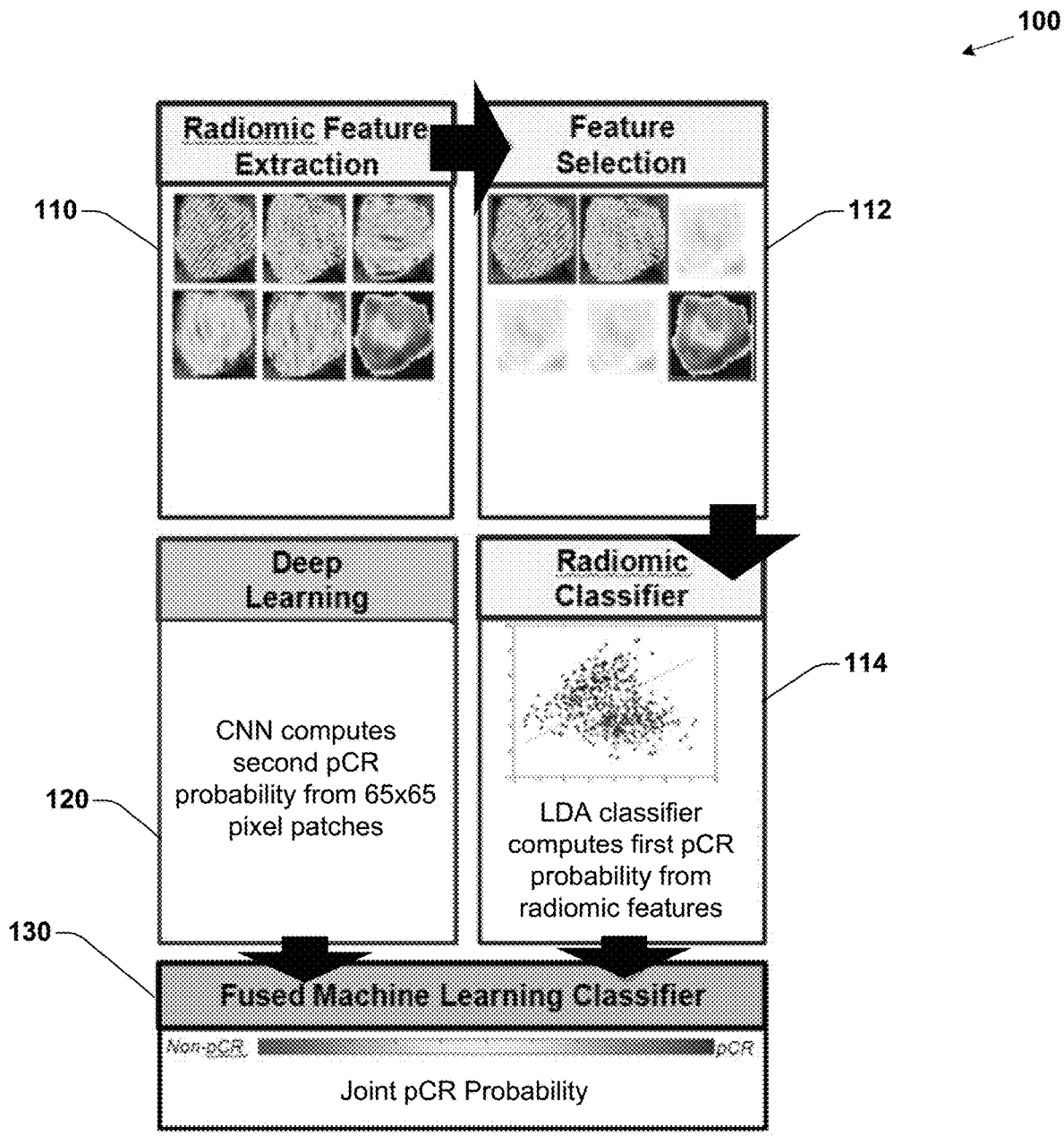
FIG. 1 illustrates a workflow for generating a combined machine learning model to predict response in BCa.

FIG. 1 illustrates an exemplary workflow 100 for generating a combined machine learning model for predicting recurrence from pre-treatment breast DCE-MRI imagery. Workflow 100 includes, at 110, extracting radiomic features from a set of pre-treatment breast DCE-MRI images that include a region of tissue demonstrating BCa pathology. A member of the set of pre-treatment breast DCE-MRI images includes a tumoral region. In this example, the set of pre-treatment breast DCE-MRI images includes DCE-MRI scans acquired of a cohort of one-hundred and sixty-six (166) patients having breast tumors >3 cm, from the ISPY-1 dataset from The Cancer Imaging Archive (TCIA). Forty-nine (49) members of the cohort experienced pCR and one-hundred and seventeen (117) did not experience pCR. In this example, fifty three (53) members of the cohort were HER2+, forty-three (43) were triple negative, sixty-six (66) were HER2−, ER+, and four were of unknown status. In this example, a set of radiomic features including two-hundred and fifteen (215) radiomic features that quantify textural heterogeneity in the tumoral region are extracted from each member of the set of pre-treatment breast DCE-MRI images respectively.

Workflow 100 also includes, at 112, selecting the most discriminatory features from among the set of radiomic features. In this example, the top eight most discriminatory features are selected using a minimum redundancy, maximum relevance (mRMR) feature selection approach. Embodiments may compute values that summarize the distribution of a radiomic feature across an entire tumor. For instance, if embodiments compute a Haralick entropy feature on a 1000 pixel tumor, we will have 1000 different Haralick entropy measurements. Embodiments may then compute first order statistics associated with those values. In this example, the top eight most discriminatory features includes a skewness of a Laws E5E5 feature, a kurtosis of a Haralick entropy feature, a kurtosis of a Laws R5R5 feature, a median of a Laws E5E5 feature, a skewness of a co-occurrence of local anisotropic gradient orientations (CoLlAGe) energy feature, a kurtosis of a Laws W5W5 feature, a kurtosis of a Gabor (W=4 px, theta=$\pi/2$) feature, and a kurtosis of a Gabor (W=2px, theta=$\pi/4$) feature. In other embodiments, other numbers of features may be selected, the top most discriminative features may include different features, other statistical representations of the radiomic features may be computed, or a different feature selection approach may be employed.

Workflow 100 also includes, at 114, training a machine learning radiomic feature-based classifier to distinguish tissue that will respond to NAC from tissue that will not respond to NAC, including but not limited to pCR. In this example, the machine learning radiomic feature-based classifier is a linear discriminant analysis (LDA) classifier trained using a training set of DCE-MRI images to predict pCR. In this example, the cohort is divided into a training set of DCE-MRI images acquired of one-hundred and thirty-three (133) patients, and a testing set of DCE-MRI images acquired of thirty-three (33) patients. In this example, also at 114, the machine learning radiomic feature-based classifier is also tested using the testing set. In another embodiment, other types of machine learning classifiers may be employed, including a support vector machine (SVM) classifier, a quadratic discriminant analysis (QDA) classifier, a decision tree or random forest classifier, a logistic regression classifier, or a diagonal linear discriminant analysis (DLDA) classifier. The machine learning radiomic feature-based classifier produces a first probability of response. In this example, the first probability ranges from 0 to 1.

Figure 2:
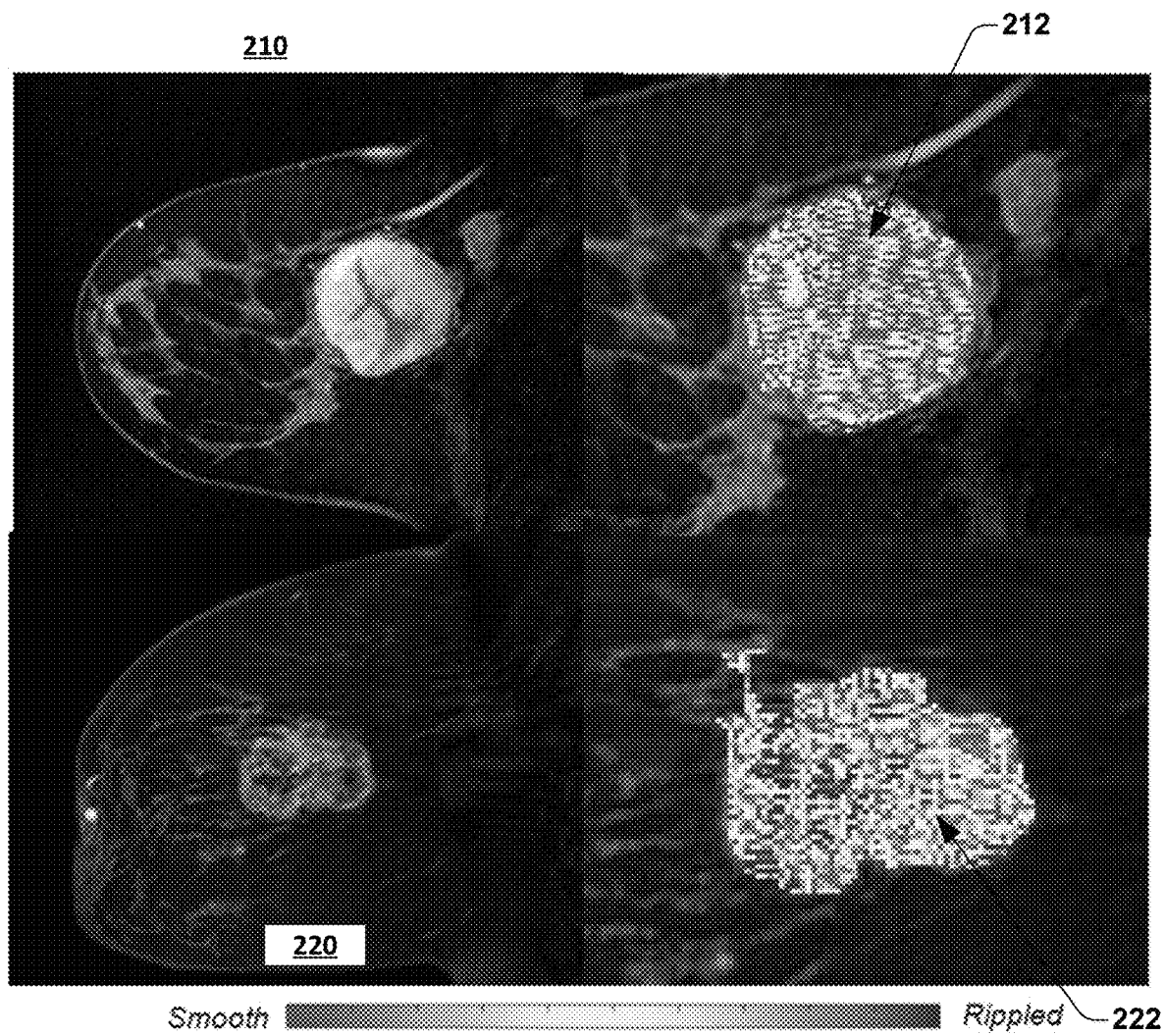
FIG. 2 illustrates heatmaps of the expression of image features that differ between patients that responded or did not respond to NAC.

FIG. 2 illustrates radiomic features of rippled enhancement detected by Laws features in a region of tissue, (e.g., a tumor) that experienced pCR and a region of tissue that did not experience pCR. FIG. 2 illustrates a first DCE-MRI image of a region of tissue (ROT) 210 that experienced pCR. FIG. 2 further illustrates a magnified section 212 of ROT 210. Magnified section 212 illustrates a rippling effect that indicates fluctuating contrast enhancement patterns. FIG. 2 also illustrates a second DCE-MRI image of a ROT 220 that did not experience pCR. FIG. 2 further illustrates a magnified section 222 of ROT 220. Magnified section 222 illustrates non-pCR tissue characterized by increased intra-tumoral rippling, as detected by Laws features.

Figure 3:
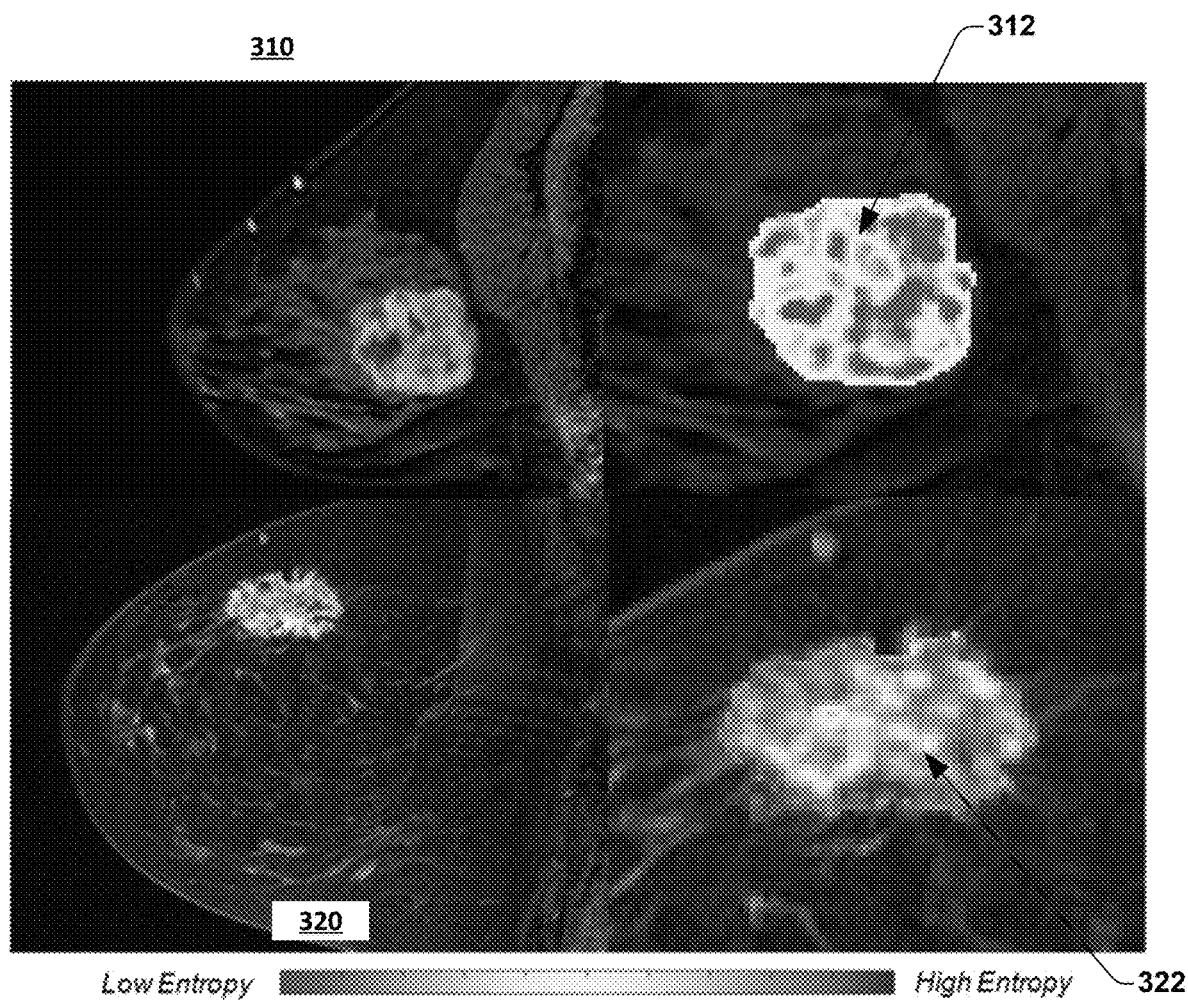
FIG. 3 illustrates heatmaps of the expression of image features that differ between patients that responded or did not respond to NAC.

FIG. 3 illustrates radiomic features of textural entropy on MRI of a region of tissue (e.g., a tumor) that experienced pCR, as compared to a region of tissue (e.g., a tumor) that did not experience pCR. FIG. 3 illustrates a first DCE-MRI image of a ROT 310 that experienced pCR. FIG. 3 further illustrates a magnified section 312 of ROT 310. Magnified section 312 illustrates entropy characterized by a high disorder or heterogeneity of signal intensity. FIG. 3 also illustrates a second DCE-MRI image of ROT 320 that did not experience pCR. FIG. 3 further illustrates a magnified section 322 of ROT 320. Magnified section 322 illustrates elevated entropy in a non-pCR patient, indicative of hypervascularity.

Workflow 100 also includes, at 120, training a deep learning classifier to distinguish tissue that will experience response from tissue that will not experience response, including but not limited to pCR. In this example, the deep learning classifier is a convolutional neural network (CNN) trained to recognize patterns of response, including pCR. In this example, the CNN is trained to predict response from 65 pixel by 65 pixel patches extracted from the training set. The CNN generates a probability, in this example, that ranges from 0 to 1 for each patch it evaluates during training. These patch-wise predictions are summarized into a second patient-wise probability based on the proportion of patches identified as associated with treatment response.

Embodiments may train the CNN classifier using the set of patches extracted from the training set. In a preferred embodiment, a CNN is trained using the extracted patches. In this example, a patch size of 65 pixels by 65 pixels is employed. Embodiments may employ a CNN having six convolutional blocks, where each convolutional operation decreases the size of the input image (i.e., patch). For example, in one embodiment, the first layer of the CNN includes convolution with a filter size of 3×3, which reduces the dimensions of the input from 65 pixels by 65 pixels to 63 pixels by 63 pixels. In this embodiment, after passing through all the layers of the CNN, the dimensions of the 65 pixel by 65 pixel input image are decreased by 64 pixels. Thus, for an input of a 65 pixel by 65 pixel patch, the output is a single pixel with a value bounded between 0 and 1. This value corresponds to the estimated probability of a patient achieving response, which may be directly compared to a binary response variable in order to train the model. In another embodiment, the CNN may be configured with other, different architectures, including different numbers of layers.

While a patch size of 65 pixels by 65 pixels is described, embodiments may employ other, different patch sizes. For example, in one embodiment, a patch having dimensions larger than 65 pixels by 65 pixels may be input, and the CNN architecture may be adjusted such that the different patch size input is reduced to a single pixel. In another embodiment, a patch having dimensions larger than 65 pixels by 65 pixels may be input, and the CNN architecture may be kept as described herein, thus producing an output that is larger than one pixel. Embodiments may adjust patch size based on a desired training time, a desired predictive accuracy, or desired execution time.

Embodiments may test a machine learning classifier using patches from imagery held out from the data used to train the machine learning classifier. In one embodiment, the CNN is trained using the extracted patches. In one embodiment, for the testing set, patches are extracted centered around each pixel within the tumoral region. In another embodiment, fewer than all the pixels within the tumoral region may be used. For example, in one embodiment, patches may be generated based on pixels spaced by a fixed amount (i.e., every other pixel), or may be generated from randomly selected pixels. For non-sampled pixels, embodiments may interpolate between predictions to produce a probability mask or heatmap. In one embodiment, a plurality of patches sufficient to cover the tumor region in a non-overlapping manner may be generated. Thus, in one example, for a 130 pixel by 130 pixel tumoral region, four 65 pixel by 65 pixel patches may be extracted.

Figure 4:
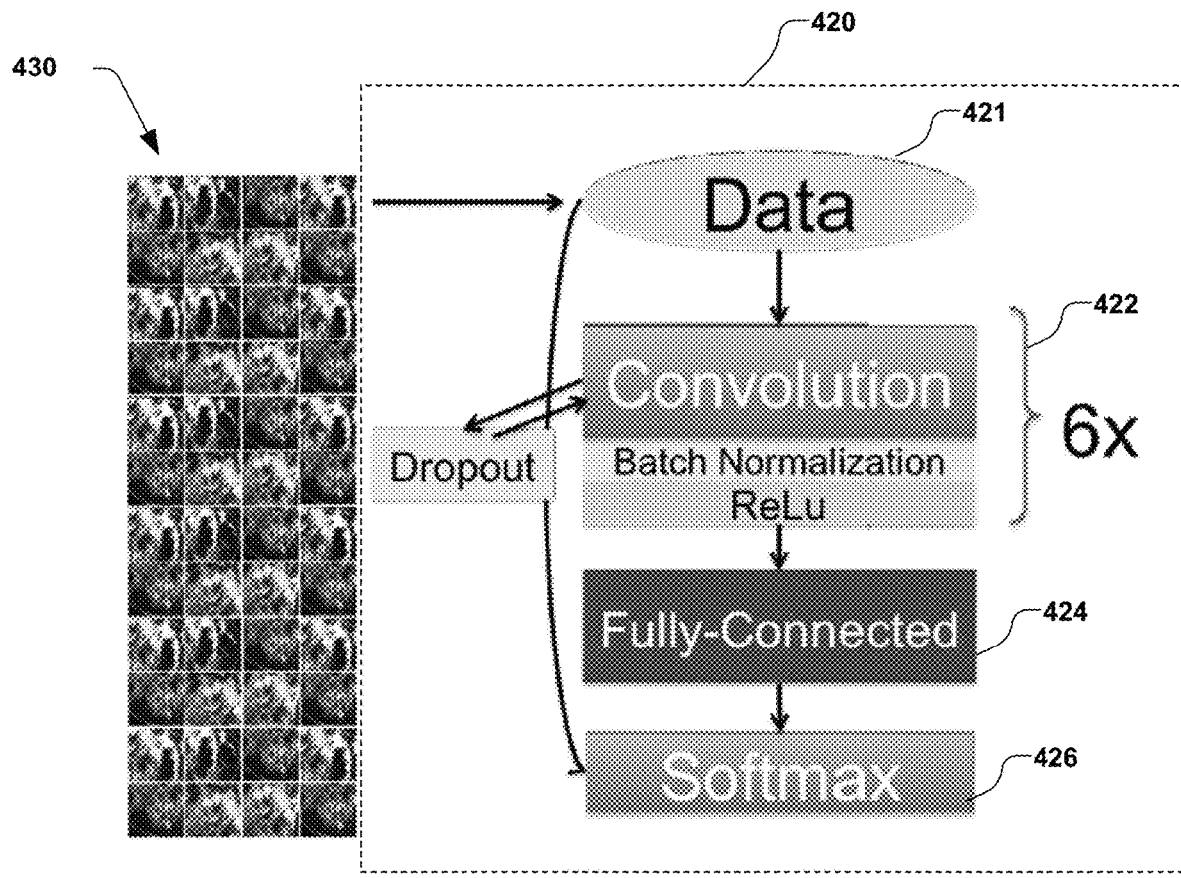
FIG. 4 illustrates an exemplary convolutional neural network (CNN) architecture.

FIG. 4 illustrates an exemplary CNN architecture 420 suitable for use by embodiments described herein. CNN architecture 420 includes receiving data 421. In this example, data 421 includes a set of patches 430 extracted from DCE-MRI imagery. In this example, a member of the set of patches has dimensions of 65 pixels by 65 pixels. CNN architecture 420 also includes, at 422, six layers, where a layer includes convolutional layers with batch normalization and ReLu activation. CNN architecture 420 also includes one fully connected layer 424. CNN architecture 420 further includes using softmax activation to determine class membership (e.g., response vs. non response, pCR vs. non-pCR). CNN architecture 420 may use random dropout or regularization to prevent overfitting during training. In another embodiment, other types of CNN architecture may be employed. For example, other, different numbers or configurations of layers may be employed, or other functions may be employed by the CNN architecture.

In one embodiment, the CNN is configured to discriminate tissue that will experience response, including but not limited to pCR following NAC from tissue that will not experience response, including but not limited to non-pCR, following NAC. In one embodiment, the CNN is a six block CNN. In this embodiment, a block has a convolution layer batch normalization and an activation function. In this embodiment, Blocks 1-5 utilize a rectified linear unit (ReLU) activation function. The final convolutional block of the CNN employs a softmax function to compute the localized patch probability by constraining it to a value between 0 and 1. In this embodiment, the CNN is trained to improve its predictions by minimizing a multinomial logistic objective loss function, a metric computing the distance between the network's predicted probability of response and a patient's binary response outcome (e.g., 0 for non-pCR, 1 for pCR). Incorrect predictions have a higher loss value, and thus information from these examples is weighted more heavily in adjusting the network towards an optimal solution. In another embodiment, the CNN may have another, different architecture. For example, in another embodiment, the CNN may have a different number of blocks or layers, or may employ other functions.

Figure 5:
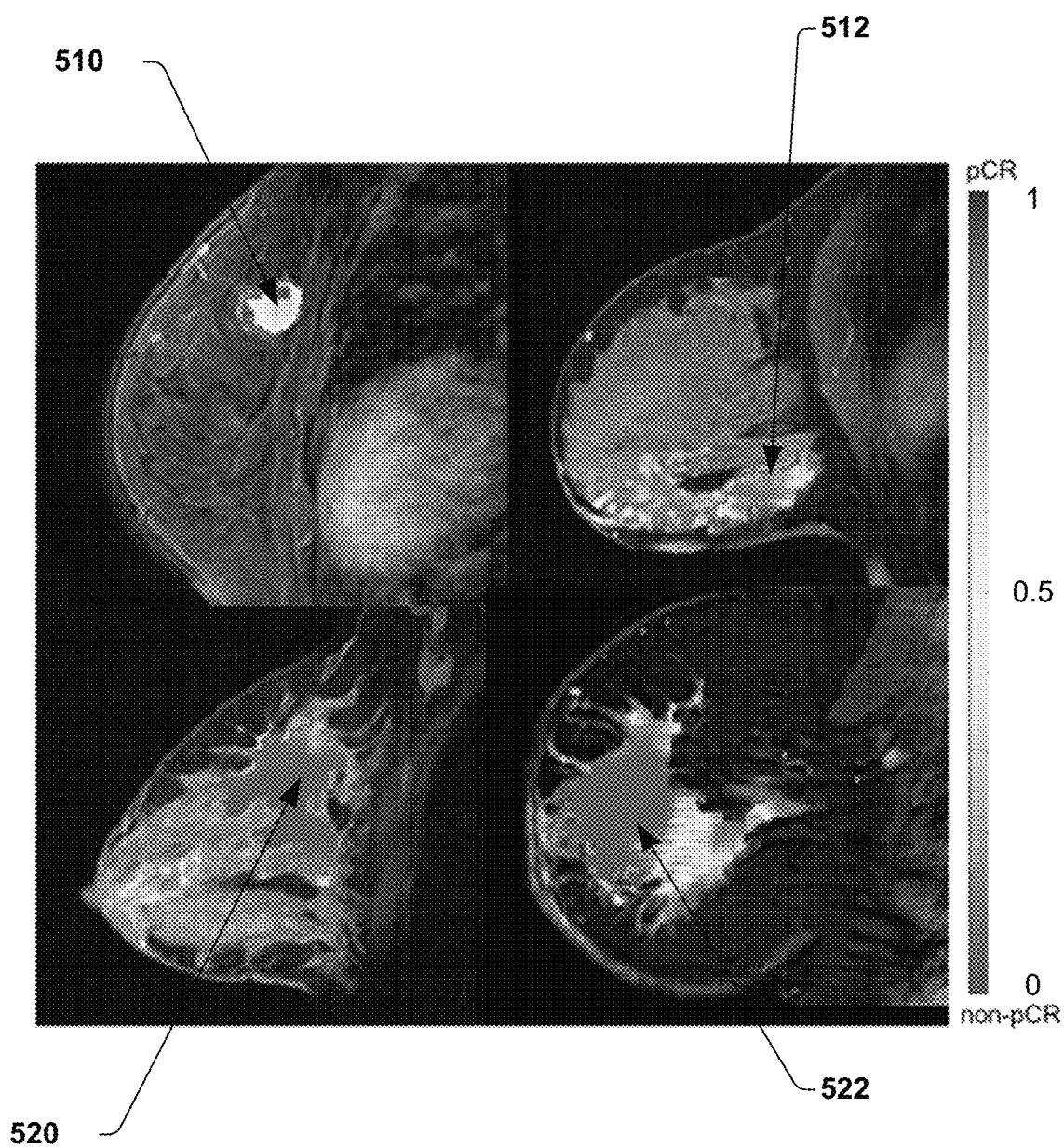
FIG. 5 illustrates heatmaps of regions predicted by a CNN as likely to respond to NAC or unlikely to respond to NAC.

FIG. 5 illustrates DCE-MRI images of pCR and non-pCR tissue classified by a CNN according to embodiments described herein. FIG. 5 illustrates, at 510 and 512, ROTs that experienced pCR. FIG. 5 also illustrates, at 520 and 522, ROTs that did not experience pCR.

Worfklow 100 also includes, at 130, generating a combined ML score based on the first probability and the second probability. In this example, the combined ML score is generated by taking the product of the first probability and the second probability. In another embodiment, the combined ML score may be generated based on the first probability and the second probability using another, different statistical approach.

Figure 6:
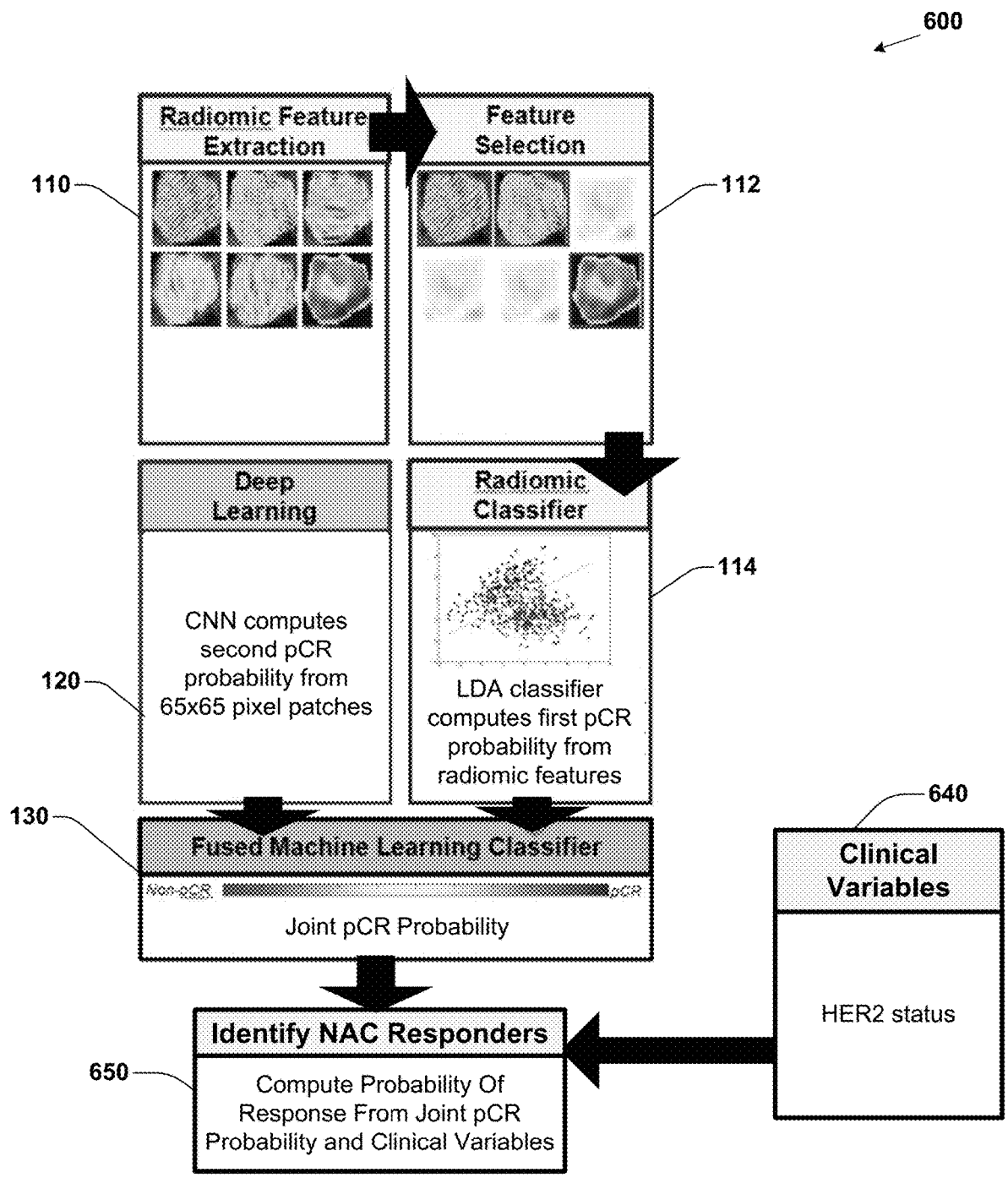
FIG. 6 illustrates a workflow for generating a model that includes clinical variables with a combined machine learning model to predict response in BCa.

While FIG. 1 illustrates an exemplary workflow for training and testing a CNN and a machine learning radiomic feature-based classifier to generate a combined ML score to distinguish tissue that will experience response from tissue that will not experience response, including but not limited to pCR, embodiments may predict response in a patient using pre-NAC DCE-MRI imagery and clinical variables. FIG. 6 illustrates an exemplary workflow 600 that is similar to workflow 100 but that includes additional details and elements. For example, the embodiment illustrated in FIG. 6 may be employed to, for a patient, predict post-NAC pCR using pre-NAC DCE-MRI imagery of the patient and a CNN classifier and LDA classifier trained as described herein. As illustrated in FIG. 6, embodiments may further access, at 640, clinical variables about the patient, and generate a NAC prediction, at 650, based on the combined ML score generated by the CNN classifier and LDA classifier, and the clinical variables. The clinical variables may include, for example, HER2 status, patient age, diameter of the tumor region, or ER/PR status. Embodiments may select the most prognostically significant clinical variable or variables using, for example, univariate analysis of the clinical variables. In one embodiment, the combined ML score may be combined with a member of the clinical variables, less than all the clinical variables, or all the clinical variables, using a multinomial regression model. The output of the multinomial regression model is, in this example, a 0 to 1 probability of response to NAC derived from the combination of the combined ML score and the clinical variable.

HER2 status alone is predictive of pCR with an AUC of 0.69, a sensitivity of 63%, and a specificity of 76%. Embodiments predict pCR from pre-treatment DCE-MRI imagery using the combined ML score alone with an AUC of at least 0.84, a sensitivity of at least 63%, and a specificity of at least 84%. Embodiments predict pCR from pre-treatment DCR-MRI imagery using the combined ML score and HER2 status with an AUC of 0.93, a sensitivity of 75%, and a specificity of 92%.

In examples described herein, response may include pCR. pCR may include pT0 ypN0, which indicates absence of invasive cancer and in situ cancer in the breast and axillary nodes. pCR may also include ypT0/is ypN0, which indicates absence of invasive cancer in the breast and axillary nodes, irrespective of carcinoma in situ. pCR may also include ypT0/is, which indicates absence of invasive cancer in the breast, irrespective of ductal carcinoma in situ or nodal involvement. Embodiments are not limited to predicting pCR, but may predict response or non-response other than pathological complete response.

Embodiments may pre-process a DCE-MRI image, including DCE-MRI images used in training and testing machine learning classifiers and CNN classifiers as described herein. A DCE-MRI image as employed herein includes a tumoral region, and may also include non-tumoral (i.e., stroma) tissue. MRI signal values may vary significantly between scanners in a way that does not reflect any biological or physical meaning in the tissue being scanned.

The intensity of each pixel in a member of a set of images is normalized to the mean intensity of a reference region of the stroma or other non-tumor tissue on the pre-contrast scan, for each patient, respectively. Embodiments thus place members of the set of images into the same relative intensity range, which is tied to biological meaning associated with the intensity of the stroma or other non-tumor tissue without contrast.

In one embodiment, following pixel-level normalization, image values for each patient are rescaled as integer values from 0 to 255 based on distribution of post-contrast intra-tumoral intensity across the set of images. In this embodiment, the pre-contrast phase and first post-contrast phase are combined into separate channels of a single image, since it is during this initial phase of imaging that the tumor is best distinguished from surrounding tissue due to the effect of enhanced permeability and retention. In another embodiment, image values for each patient may be rescaled as integer values of another, different range. Embodiments may provide as input to the CNN the post-contrast image, or a combination of images from different phases (e.g., pre-contrast, first post-contrast, later post-contrast phases) of the DCE-MRI scan.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, calculating, determining, and so on, refer to actions and processes of a computer system, logic, circuit, processor, or similar electronic device that manipulates and transforms data represented as physical (electronic) quantities.

Example methods and operations may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

Figure 7:
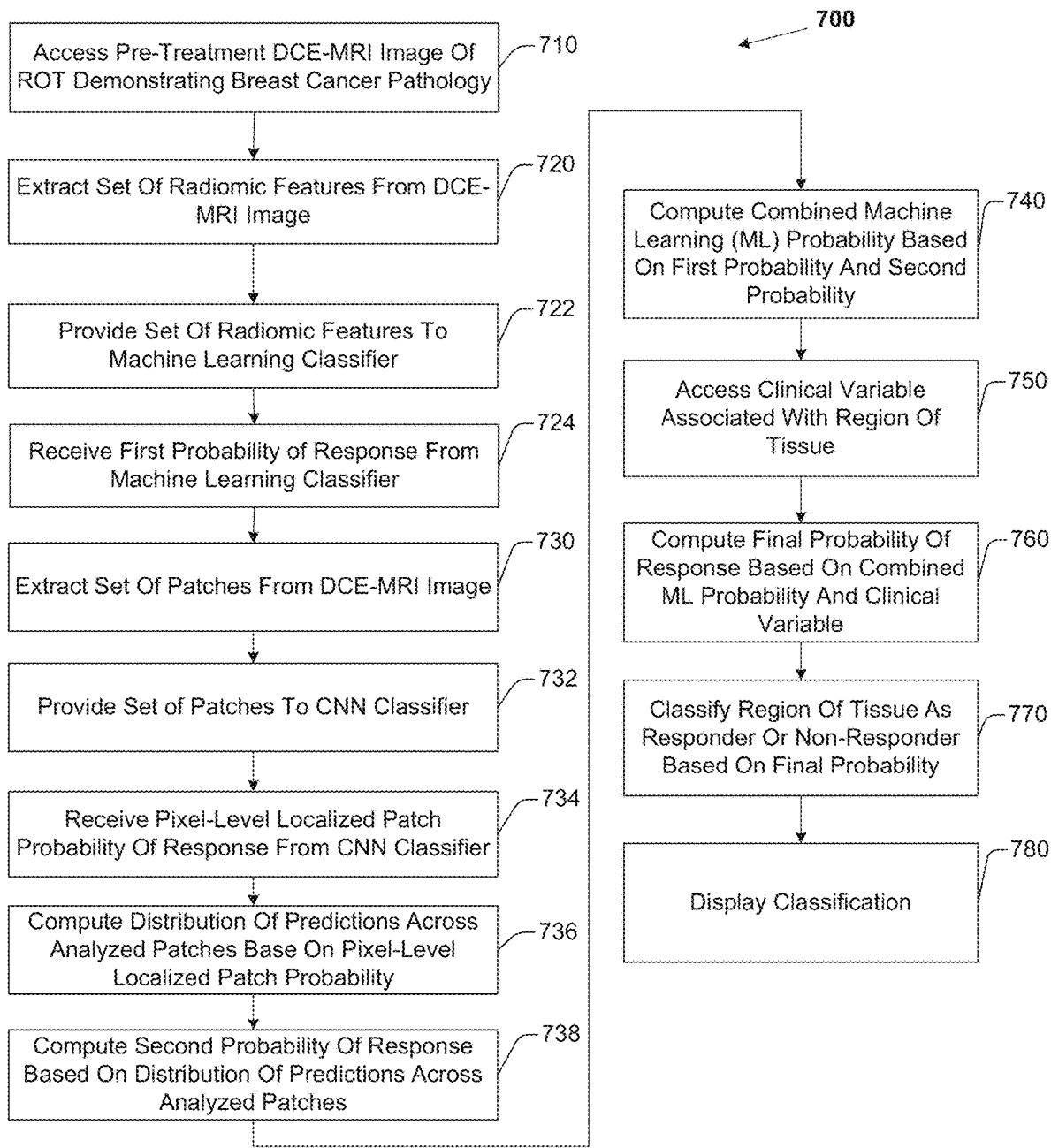
FIG. 7 is a flow diagram of operations for predicting response in BCa.

FIG. 7 is a flow diagram of example operations 700 that may be performed by a processor for predicting response to neoadjuvant chemotherapy (NAC) in breast cancer (BCa). A processor(s) may include any combination of general-purpose processors and dedicated processors (e.g., graphics processors, application processors, etc.). The processors may be coupled with or may include memory or storage and may be configured to execute instructions stored in the memory or storage to enable various apparatus, applications, or operating systems to perform the operations. The memory or storage devices may include main memory, disk storage, or any suitable combination thereof. The memory or storage devices may include, but are not limited to any type of volatile or non-volatile memory such as dynamic random access memory (DRAM), static random-access memory (SRAM), erasable programmable read-only memory (EPROM), electrically erasable programmable read-only memory (EEPROM), Flash memory, or solid-state storage.

The set of operations 700 includes, at 710, accessing an image of a region of tissue. The region of tissue may include breast tissue. The image may be a digitized image of a region of tissue demonstrating BCa. The region of tissue includes a tumoral region, and the image includes a representation of the tumoral region. Accessing the image includes acquiring electronic data, reading from a computer file, receiving a computer file, reading from a computer memory, or other computerized activity not practically performed in the human mind. A member of the set of images has a plurality of pixels, a pixel having an intensity. In one embodiment, the image is a pre-treatment dynamic contrast enhanced magnetic resonance imaging (DCE-MRI) image. In one embodiment, the pre-treatment DCE-MRI image has dimensions of 512 pixels by 512 pixels. In another embodiment, the pre-NAC DCE-MRI image may have other, different imaging parameters, including different dimensions. While 512 pixel by 512 pixel DCE-MRI images acquired using a 1.5 T or 3 T magnet and a four-channel MRI coil or eight-channel MRI coil are described in this example, images having other imaging parameters may be employed.

The set of operations 700 also includes, at 720, extracting a set of radiomic features from the tumoral region represented in the image. In one embodiment, the set of radiomic features includes eight radiomic features. Embodiments may compute statistical features of the radiomic features, including first-order statistics. In one embodiment, the set of radiomic features includes a skewness of a Laws E5E5 feature; a kurtosis of a Haralick entropy feature; a kurtosis of a Laws R5R5 feature; a median of a Laws E5E5 feature; a skewness of a co-occurrence of local anisotropic gradient orientations (CoLlAGe) energy feature; a kurtosis of a Laws W5W5 feature; a kurtosis of a first Gabor feature; and a kurtosis of a second, different Gabor feature. In another embodiment, the set of radiomic features may include other, different radiomic features, or another, different number of radiomic features. Extracting the set of radiomic features includes acquiring electronic data, reading from a computer file, receiving a computer file, reading from a computer memory, or other computerized activity not practically performed in the human mind.

The set of operations 700 also includes, at 722, providing the set of radiomic features to a machine learning classifier. The machine learning classifier is configured to distinguish tissue that will respond to chemotherapy from tissue that will not respond to chemotherapy. In one embodiment, the machine learning classifier is a linear discriminant analysis (LDA) classifier. In another embodiment, the machine learning classifier may be another different type of machine learning classifier, including, for example, a quadratic discriminant analysis (QDA) classifier, a support vector machine (SVM) classifier, or a random forests classifier. Providing the set of radiomic features to the machine learning classifier includes acquiring electronic data, reading from a computer file, receiving a computer file, reading from a computer memory, or other computerized activity not practically performed in the human mind.

The set of operations 700 also includes, at 724, receiving, from the machine learning classifier, a first probability of response based on the set of radiomic features. The first probability of response may, in one embodiment, be a value ranging from 0 to 1. Receiving, from the machine learning classifier, a first probability of response, includes acquiring electronic data, reading from a computer file, receiving a computer file, reading from a computer memory, or other computerized activity not practically performed in the human mind. The first probability of response may be a probability of pCR, or of another degree of response.

The set of operations 700 also includes, at 730, extracting a set of patches from the tumoral region represented in the image. In one embodiment, the set of patches includes, for each pixel of the tumoral region respectively, a patch centered around the pixel. Embodiments may select patches centered around fewer than all the pixels in the tumoral region. Thus, in another embodiment, the set of patches includes, for a threshold number of pixels that is smaller than the total number of the pixels in the tumoral region, a patch centered around a member of the threshold number of pixels. In one embodiment, a member of the threshold number of pixels is selected based on a response predictability level of the pixel, where a pixel having a higher response predictability level is more likely to be selected than a pixel having a lower response predictability level. In another embodiment, the threshold number of pixels may be user defined, may be defined based on desired performance levels, or may be defined based on available computational resources. In another embodiment, a member of the threshold number of pixels is selected based on a selection pattern. A selection pattern may define, for example, that every other pixel is selected, or that every third pixel is selected. Extracting the set of patches includes acquiring electronic data, reading from a computer file, receiving a computer file, reading from a computer memory, or other computerized activity not practically performed in the human mind.

In one embodiment, a patch has dimensions of 65 pixels by 65 pixels. In another embodiment, a patch may have other, different dimensions. For example, a patch may have dimensions smaller than 65 pixels, or larger than 65 pixels. Patch size may be user selectable. A patch size may be selected based on available computational resources. A patch size may be selected based on properties of the CNN. For example, a first CNN may be configured to analyze patches of 65 pixels by 65 pixels and output a one-pixel output. A second, different CNN may be configured to analyze patches having larger dimensions (e.g., 100 pixels by 100 pixels), or smaller dimensions, and output a one-pixel output. In yet another embodiment, a third, different CNN may be configured to analyze patches having different dimensions (e.g., 100 pixels by 100 pixels, or 65 pixels by 65 pixels) and to output different sized outputs.

The set of operations 700 also includes, at 732, providing the set of patches to a convolutional neural network (CNN). The CNN is configured to distinguish tissue that will respond to chemotherapy from tissue that will not respond to chemotherapy based, at least in part, on the set of patches. Chemotherapy may include, for example, NAC. Providing the set of patches to the CNN includes acquiring electronic data, reading from a computer file, receiving a computer file, reading from a computer memory, or other computerized activity not practically performed in the human mind.

The set of operations 700 also includes, at 734, receiving, from the CNN, a pixel-level localized patch probability of response. The CNN computes the pixel-level localized patch probability based, at least in part, on the set of patches. In one embodiment, the CNN is configured to accept a 65 pixel by 65 pixel patch as input, and to output a one-pixel output as a pixel-level localized patch probability. In one embodiment, the pixel-level localized patch probability is a value ranging from 0 to 1. Receiving, from the CNN, the pixel-level localized patch probability includes acquiring electronic data, reading from a computer file, receiving a computer file, reading from a computer memory, or other computerized activity not practically performed in the human mind.

The CNN is configured to discriminate tissue that will experience response, including but not limited to pCR, post-NAC, from tissue that will not experience response, including but not limited to pCR, post-NAC. In one embodiment, the CNN is a six block CNN. In this embodiment, a block has a convolution layer batch normalization and an activation function. In this embodiment, Blocks 1-5 utilize a rectified linear unit (ReLU) activation function. The final convolutional block of the CNN employs a softmax function to compute the localized patch probability by constraining it to a value between 0 and 1. In this embodiment, the CNN is trained to improve its predictions by minimizing a multinomial logistic objective loss function, a metric computing the distance between the network's predicted probability of response and a patient's binary response outcome (e.g., 0 for non-pCR, 1 for pCR). Incorrect predictions have a higher loss value, and thus information from these examples are weighted more heavily in adjusting the network towards an optimal solution. In another embodiment, the CNN may have another, different architecture. For example, in another embodiment, the CNN may have a different number of blocks or layers, or may employ other functions.

The set of operations 700 also includes, at 736, computing a distribution of predictions across analyzed patches based on the pixel-level localized patch probability. Computing the distribution of predictions includes acquiring electronic data, reading from a computer file, receiving a computer file, reading from a computer memory, or other computerized activity not practically performed in the human mind.

The set of operations 700 also includes, at 738, computing a second probability of response based on the distribution of predictions. In one embodiment, computing the second probability of response based, at least in part, on the distribution of predictions across analyzed patches, includes computing the second probability of response using a majority voting scheme. In this embodiment, upon determining that at least 50% of the pixels in the distribution of predictions across analyzed patches are more likely to experience response than not, the region of tissue is classified as a responder. In another embodiment, other classification schemes may be employed. For example, the region of tissue may be classified as a responder when at least 60% of the pixels in the distribution of predictions across analyzed patches are more likely to experience pCR than not. Embodiments may generate a patient-wise probability of response based on the distribution of predictions, or may classify the patient as a responder or non-responder based on the distribution of predictions or the second probability. Computing the second probability includes acquiring electronic data, reading from a computer file, receiving a computer file, reading from a computer memory, or other computerized activity not practically performed in the human mind.

The set of operations 700 also includes, at 740, computing a combined machine learning (ML) probability from the first probability and the second probability. In one embodiment, computing the combined ML probability includes computing the product of the first probability and the second probability. In another embodiment, the combined ML probability may be computed using another, different technique. Computing the combined ML probability includes acquiring electronic data, reading from a computer file, receiving a computer file, reading from a computer memory, or other computerized activity not practically performed in the human mind.

The set of operations 700 also includes, at 750, accessing a clinical variable associated with the region of tissue. In one embodiment, the clinical variable is an HER2 status associated with the region of tissue. In another embodiment, the clinical variable may further include an age of the patient of which the image is acquired, a diameter of the tumoral region, or a hormone receptor status. The clinical variable may be associated with the patient on a patient-wise level. Embodiments may select a clinical variable based on a univariate analysis of differences in clinical variables between responders and non-responders. Accessing the clinical variable includes acquiring electronic data, reading from a computer file, receiving a computer file, reading from a computer memory, or other computerized activity not practically performed in the human mind.

The set of operations 700 also includes, at 760, computing a final probability of response based on the combined ML probability and the clinical variable. In one embodiment, the final probability is computed using a multinomial logistic regression model that outputs a probability on a range of 0 through 1. Computing the final probability includes acquiring electronic data, reading from a computer file, receiving a computer file, reading from a computer memory, or other computerized activity not practically performed in the human mind.

The set of operations 700 also includes, at 770, generating a classification of the region of tissue as a responder or non-responder based, at least in part, on the final probability of response. In one embodiment, upon determining that the final probability of response is greater than or equal to 0.5, the region of tissue is classified as a responder. Embodiments may generate a classification of the patient of which the imagery is acquired as a responder or non-responder based, at least in part, on the final probability of response. Upon determining that the final probability is less than 0.5, the region of tissue is classified as a non-responder. In another embodiment, other classification schemes may be employed. Generating the classification includes acquiring electronic data, reading from a computer file, receiving a computer file, reading from a computer memory, or other computerized activity not practically performed in the human mind.

The set of operations 700 further includes, at 780, displaying the classification. Displaying the classification may include displaying the classification on a computer monitor, a smartphone display, a tablet display, or other displays. Displaying the classification may also include printing the classification. Displaying the classification may also include controlling a response prediction system, a personalized medicine system, a monitor, or other display, to display operating parameters or characteristics of a machine learning classifier or a deep learning classifier, during both training and testing, or during clinical operation of the machine learning classifier or deep learning classifier. By displaying the classification, example embodiments provide a timely and intuitive way for a human medical practitioner to more accurately classify a region of tissue (or patient) represented in DCE-MRI images as likely to respond, including but not limited to pCR, or unlikely to respond, including but not limited to pCR, thus improving on existing approaches to predicting response, including pCR, that rely on non-purpose built CNNs or other machine learning techniques. Embodiments may further display the radiological image, including a pre-contrast image or a post-contrast image. Embodiments may further display operating parameters of the CNN. Embodiments may further display a member of the set of patches, the set of radiomic features, the first probability, the second probability, or the combined ML probability.

In one embodiment, the set of operations 700 further includes controlling a processor or a personalized BCa treatment plan system to generate a personalized treatment plan. The personalized treatment plan is based, at least in part, on the classification. In one embodiment, the personalized treatment plan is further based on the images, the first probability, the second probability, or the combined ML probability. Generating a personalized treatment plan facilitates delivering a particular treatment that will be therapeutically active to the patient, while minimizing negative or adverse effects experienced by the patient. For example, the personalized treatment plan may suggest a surgical treatment, may define an immunotherapy agent, dosage, or schedule, or a chemotherapy agent dosage or schedule, when the region of tissue is classified as likely to respond. For a region of tissue classified as unlikely to respond, other treatments may be suggested.

Figure 8:
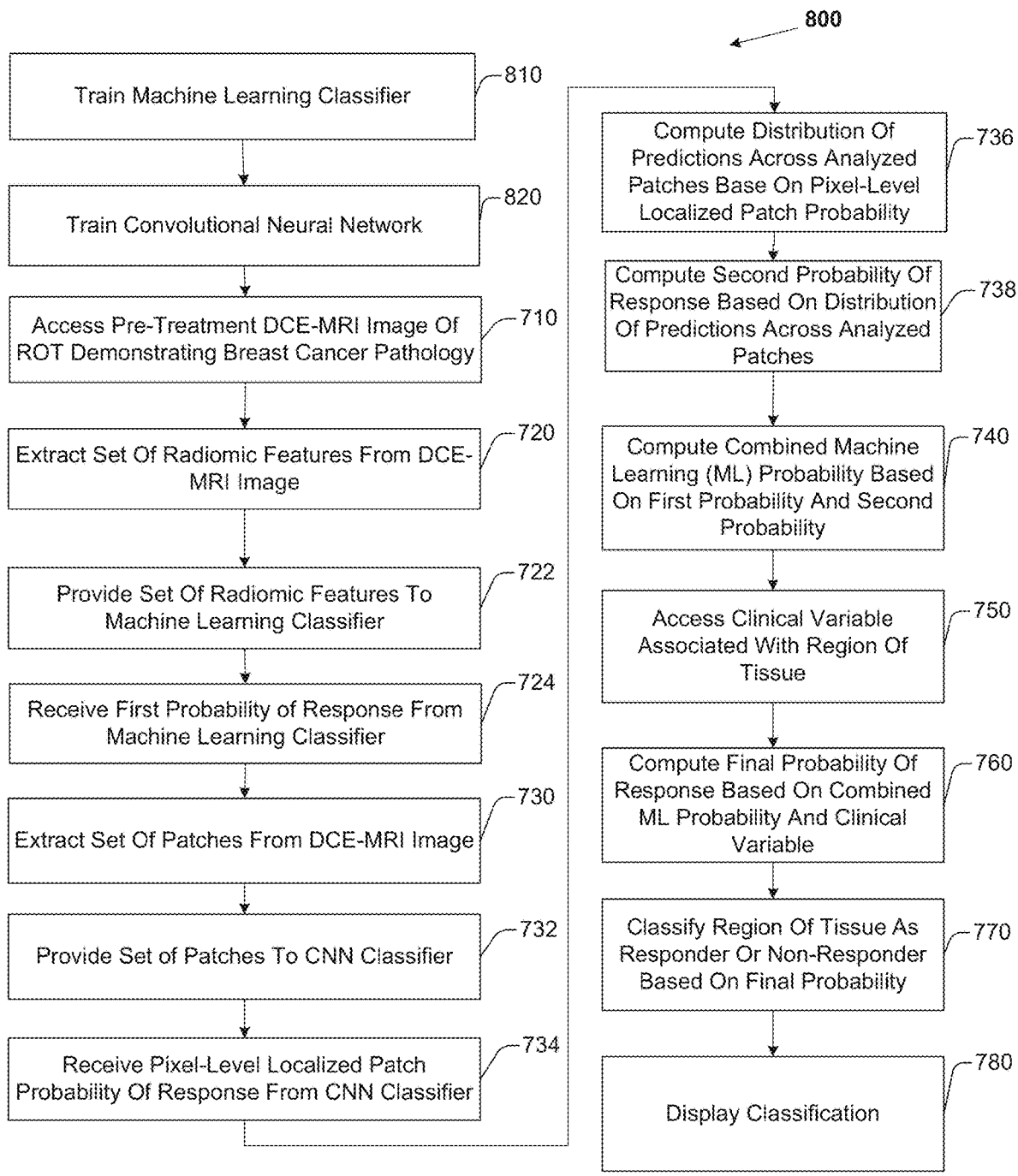
FIG. 8 is a flow diagram of operations for predicting response in BCa.

FIG. 8 illustrates operations 800 that are similar to operations 700 but that include additional details and elements. In one embodiment, the operations 800 include, at 810, training the machine learning classifier. In this embodiment, the machine learning classifier is trained and tested using a training set of images and a testing set of images. The response status of the patients of which the members of the testing set and training set are acquired is known, and clinical variables associated with the patients are also known. Training the machine learning classifier may include training the machine learning classifier until a threshold level of accuracy is achieved, until a threshold time has been spent training the machine learning classifier, until a threshold amount of computational resources have been expended training the machine learning classifier, or until a user terminates training. Other training termination conditions may be employed. Training the machine learning classifier may also include determining which radiomic features are most discriminative in distinguishing tissue likely to respond to from tissue unlikely to respond. Training the machine learning classifier may also include determining settings outside the machine learning classifier architecture but relevant to its learning behavior.

Operations 800 include, at 820, training the convolutional neural network (CNN). In this embodiment, the CNN classifier is trained and tested using a training set of images and a testing set of images. The response status of, and clinical variables associated with, the patients of which the members of the testing set and training set are acquired is known. Training the CNN classifier may include training the CNN classifier until a threshold level of accuracy is achieved, until a threshold time has been spent training the CNN classifier, until a threshold amount of computational resources have been expended training the CNN classifier, or until a user terminates training. Other training termination conditions may be employed. Training the CNN classifier may also include determining which regions of the tumoral region from which patches may be extracted are most predictive in distinguishing tissue likely to respond from tissue unlikely to respond. Training the machine learning classifier may also include determining which patch size, or number of patches, or region of a tumoral region, is most discriminative in distinguishing a positive class from a negative class (e.g., responder vs. non-responder, pCR vs. non-pCR), as well as determining settings outside the CNN architecture but relevant to its learning behavior (e.g. learning rate, the number of patches used to update the network at a single time, use of dropout and regularization).

While FIGS. 7 and 8 illustrates various actions occurring in serial, it is to be appreciated that various actions illustrated in FIG. 7 or 8 could occur substantially in parallel. By way of illustration, a first process could involve extracting radiomic features, a second process could involve extracting patches, and a third process could involve accessing a clinical variable. While three processes are described, it is to be appreciated that a greater or lesser number of processes could be employed and that lightweight processes, regular processes, threads, and other approaches could be employed.

In one example, a method may be implemented as computer executable instructions. Thus, in one example, a computer-readable storage device may store computer executable instructions that if executed by a machine (e.g., computer, processor) cause the machine to perform methods or operations described or claimed herein including operations 700 or 800 or method 1200. While executable instructions associated with the listed methods are described as being stored on a computer-readable storage device, it is to be appreciated that executable instructions associated with other example methods or operations described or claimed herein may also be stored on a computer-readable storage device. In different embodiments the example methods or operations described herein may be triggered in different ways. In one embodiment, a method or operation may be triggered manually by a user. In another example, a method or operation may be triggered automatically.

Improved classification of patients or tissue demonstrating BCa may produce the technical effect of improving treatment efficacy by increasing the accuracy of and decreasing the time required to treat patients demonstrating BCa, or other forms of cancerous pathology. Treatments and resources, including expensive immunotherapy agents or chemotherapy may be more accurately tailored to patients with a likelihood of benefiting from said treatments and resources, including responding to immunotherapy or chemotherapy, so that more appropriate treatment protocols may be employed, and expensive resources are not wasted. Controlling a personalized medicine system, a CADx system, a processor, or BCa response prediction system based on improved, more accurate identification or classification of tissue further improves the operation of the system, processor, or apparatus, since the accuracy of the system, processor, or apparatus is increased and unnecessary operations will not be performed. Embodiments described herein, including at least the sets of operations 700 and 800, apparatus 900 and 1000, and method 1200, resolve features extracted from DCE-MRI images at a higher order or higher level than a human can resolve in the human mind or with pencil and paper. For example, the radiomic features are not biological properties of cancerous tissue that a human eye can perceive. A tumor does not include an entropy feature or a Gabor feature, and these features cannot be stored in a human mind or practically computed in the human mind from digital computer files. Embodiments described herein use a combined order of specific rules, elements, operations, or components that render information into a specific format that is then used and applied to create desired results more accurately, more consistently, and with greater reliability than existing approaches, thereby improving the performance of the computer or system with which embodiments are implemented.

Using a more appropriately modulated treatment may lead to less aggressive therapeutics being required for a patient or may lead to avoiding or delaying a biopsy, a resection, or other invasive procedure. When patients demonstrating BCa who are likely to respond are more accurately distinguished from patients who are unlikely to respond, patients most at risk may receive a higher proportion of scarce resources (e.g., therapeutics, physician time and attention, hospital beds) while those less likely to benefit from the treatment, or less in need, may be spared unnecessary treatment, which in turn spares unnecessary expenditures and resource consumption. Example methods, apparatus, and other embodiments may thus have the additional technical effect of improving patient outcomes compared to existing approaches.

In one example, a method may be implemented as computer executable instructions. Thus, in one example, a computer-readable storage device may store computer executable instructions that if executed by a machine (e.g., computer, processor) cause the machine to perform methods or operations described or claimed herein including operations 700 or 800, method 1200, or any other methods or operations described herein. While executable instructions associated with the listed methods are described as being stored on a computer-readable storage device, it is to be appreciated that executable instructions associated with other example methods or operations described or claimed herein may also be stored on a computer-readable storage device. In different embodiments the example methods or operations described herein may be triggered in different ways. In one embodiment, a method or operation may be triggered manually by a user. In another example, a method or operation may be triggered automatically.

Figure 9:
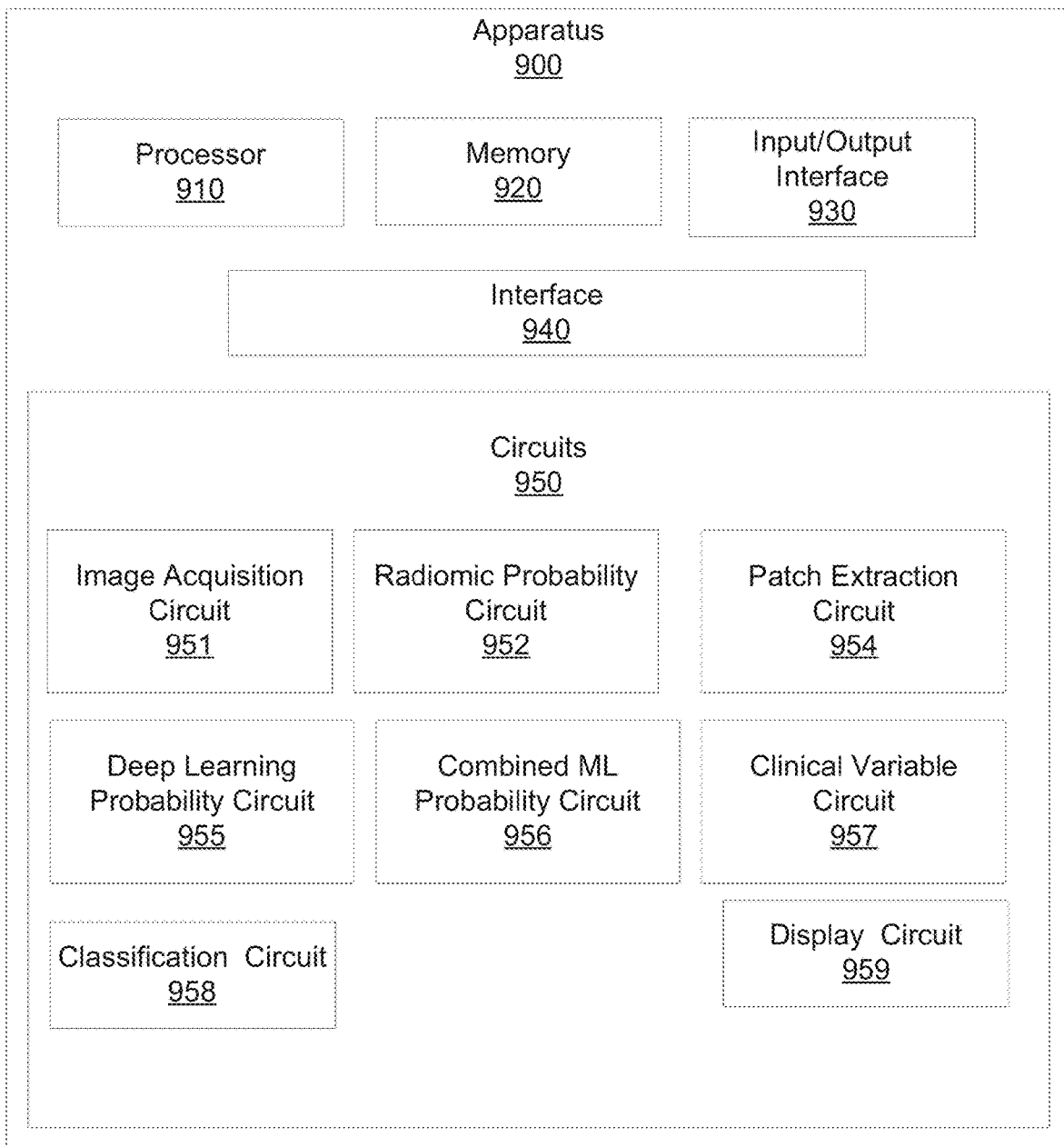
FIG. 9 illustrates an example apparatus for predicting response in BCa.

FIG. 9 illustrates an example apparatus 900 for predicting response to neo-adjuvant chemotherapy in breast cancer. Apparatus 900 includes a processor 910. Apparatus 900 also includes a memory 920. Processor 910 may, in one embodiment, include circuitry such as, but not limited to, one or more single-core or multi-core processors. Processor 910 may include any combination of general-purpose processors and dedicated processors (e.g., graphics processors, application processors, etc.). The processors may be coupled with or may include memory (e.g. memory 920) or storage and may be configured to execute instructions stored in the memory or storage to enable various apparatus, applications, or operating systems to perform the operations. Memory 920 is configured to store a DCE-MRI image of a region of tissue demonstrating BCa. The image has a plurality of pixels, a pixel having an intensity. Memory 920 may be further configured to store a training set of DCE-MRI images of tissue demonstrating BCa, or a testing set of DCE-MRI images of tissue demonstrating BCa. Memory 920 may be further configured to store clinical variables associated with a patient of whom a DCE-MRI image is acquired.

Apparatus 900 also includes an input/output (I/O) interface 930, a set of circuits 950, and an interface 940 that connects the processor 910, the memory 920, the I/O interface 930, and the set of circuits 950. I/O interface 930 may be configured to transfer data between memory 920, processor 910, circuits 950, and external devices, for example, a CADx system or a personalized medicine system.

The set of circuits 950 includes an image acquisition circuit 951, a radiomic probability circuit 952, a patch extraction circuit 954, a deep learning probability circuit 955, a combined machine learning (ML) probability circuit 956, a clinical variable circuit 957, a classification circuit 958, and a display circuit 959.

Image acquisition circuit 951 is configured to access a diagnostic DCE-MRI image of a region of tissue demonstrating BCa. The region of tissue includes a tumoral region. Accessing the diagnostic image may include accessing a digitized image of DCE-MRI image of a region of tissue demonstrating BCa stored in memory 920. Accessing the diagnostic DCE-MRI image includes acquiring electronic data, reading from a computer file, receiving a computer file, reading from a computer memory, or other computerized activity that cannot practically be performed in the human mind.

Radiomic probability circuit 952 is configured to extract a set of radiomic features from the tumoral region represented in the diagnostic DCE-MRI image. Radiomic probability circuit 952 is further configured to compute a first probability that the region of tissue will experience response based on the set of radiomic features.

In one embodiment, the set of radiomic features includes eight radiomic features. In one embodiment, the set of radiomic features includes a skewness of a Laws E5E5 feature; a kurtosis of a Haralick entropy feature; a kurtosis of a Laws R5R5 feature; a median of a Laws E5E5 feature; a skewness of a co-occurrence of local anisotropic gradient orientations (CoLlAGe) energy feature; a kurtosis of a Laws W5W5 feature; a kurtosis of a first Gabor feature; and a kurtosis of a second, different Gabor feature. In another embodiment, the set of radiomic features may include other, different radiomic features, or another, different number of radiomic features.

In one embodiment, radiomic probability circuit 952 is configured as a linear discriminant analysis (LDA) classifier. In another embodiment, radiomic probability circuit 952 may be configured as another, different type of machine learning classifier, including, for example, a quadratic discriminant analysis (QDA) classifier, a support vector machine (SVM) classifier, or a random forest classifier.

Patch extraction circuit 954 is configured to extract a set of patches from the tumoral region. In one embodiment, patch extraction circuit 954 is configured to, for each pixel in the tumoral region, extract a patch centered on each pixel, respectively. In another embodiment, patch extraction circuit 954 may be configured to, for a threshold number of pixels in the tumoral region, extract a patch centered on each of the threshold number of pixels, respectively. In one embodiment, the threshold number of pixels is less than number of pixels in the tumoral region. In one embodiment, a member of the threshold number of pixels is selected based on a response predictability level of the pixel. In another embodiment, the threshold number of pixels may be, for example, 50% of the number of pixels, one-third of the number of pixels, or some other number that is less than the total number of pixels in the tumoral region.

Deep learning probability circuit 955 is configured to compute a pixel-level probability that the region of tissue will experience response post-NAC. Deep learning probability circuit 955 is configured to compute the pixel-level probability based, at least in part, on the set of patches. Deep learning probability circuit 955 is further configured to compute a second probability the region of tissue will experience response post-NAC based on the pixel-level probability.

In one embodiment, deep learning probability circuit 955 is configured as a CNN having six blocks. In this embodiment, a block has a convolution layer having batch normalization and a rectified linear unit (ReLU) on blocks 1-5. The CNN employs a multinomial logistic objective loss function for optimization during training. The CNN computes the pixel-level probability using a softmax function on the final block. In another embodiment, deep learning probability circuit 955 may be configured with another, different CNN architecture.

Combined machine learning (ML) probability circuit 956 is configured to compute a combined ML score based on the first probability and the second probability. In one embodiment, combined ML probability circuit 956 is configured to compute the combined ML score based on a product of the first probability and the second probability. In another embodiment, combined ML probability circuit 956 is configured to compute the combined ML score based on the first probability and the second probability using a different technique.

Clinical variable circuit 957 is configured to access a clinical variable associated with the region of tissue. In one embodiment, the clinical variable is HER2 status of the tumor represented in the region of tissue represented in the diagnostic DCE-MRI image. The clinical variable may be a patient-level clinical variable. In another embodiment, the clinical variable may include an age of the patient of which the image is acquired, a diameter of the tumoral region, a hormone receptor status, or other clinical variable.

Classification circuit 958 is configured to generate a classification of the region of tissue as a responder or non-responder. Classification circuit 958 generates the classification based, at least in part, on the combined ML score and the clinical variable. In another embodiment, classification circuit 958 may classify the region of tissue according to another, different classification scheme. For example, classification circuit 958 may be configured, in one embodiment, to classify a region of tissue as "responder", "non-responder", or "unknown". Other classification schemes may be employed. Classification circuit 958 may be configured to generate a classification of the patient of which the region of tissue was acquired, as a responder or non-responder, based on the combined ML score and the clinical variable.

Display circuit 959 is configured to display the classification. In one embodiment, display circuit 959 is configured to display the classification on a computer monitor, a smartphone display, a tablet display, or other displays. Displaying the classification may also include printing the classification. Display circuit 959 may also control a CADx system, a monitor, or other display, to display operating parameters or characteristics of members of circuit 950, including radiomic probability circuit 952 or deep learning probability circuit 955, including a machine learning classifier, during both training and testing, or during clinical operation of apparatus 900 or other embodiments described herein Display circuit 959 may be further configured to display the diagnostic DCE-MRI image, the set of radiomic features, the set of patches, the first probability, the second probability, the combined ML probability, or the clinical variable.

Figure 10:
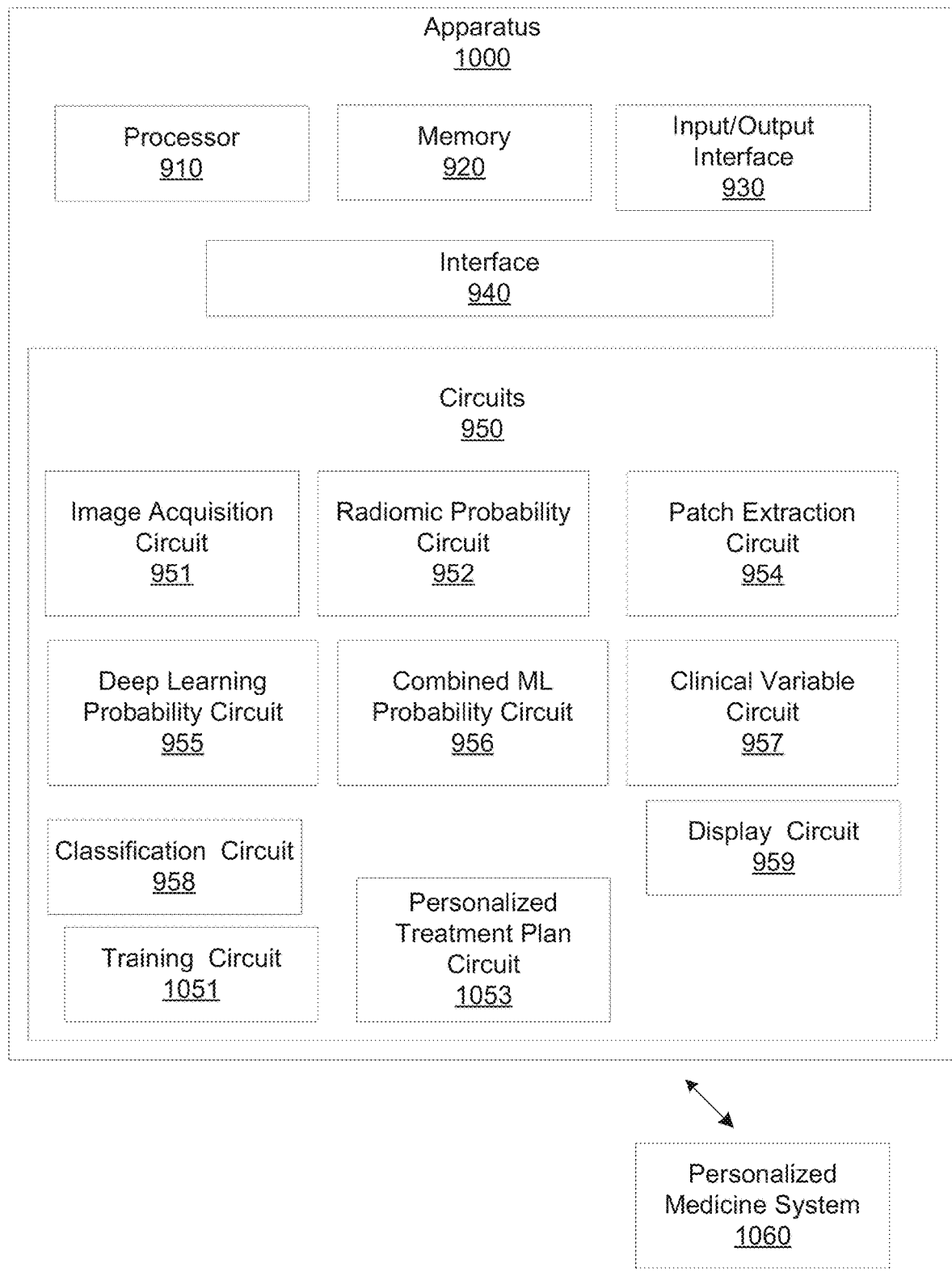
FIG. 10 illustrates an example apparatus for predicting response in BCa.

FIG. 10 illustrates an apparatus 1000 that is similar to apparatus 900 but that includes additional elements and details. Apparatus 1000 includes a personalized treatment plan circuit 1053. Personalized treatment plan circuit 1053 is configured to generate a personalized treatment plan based, at least in part, on the classification. In one embodiment, the personalized treatment plan is further based on the diagnostic DCE-MRI image, the radiomic features, the set of patches, the first probability, the second probability, the combined ML probability, or the clinical variable or variables. The personalized treatment plan may suggest a surgical treatment, may define an immunotherapy agent dosage or schedule, or a chemotherapy agent dosage or schedule, when the region of tissue is classified as likely to respond to treatment, including NAC. For a region of tissue classified as unlikely to respond to treatment, including NAC, other treatments, schedules, or dosages may be suggested.

In one embodiment, apparatus 1000 also includes training circuit 1051. Training circuit 1051 is configured to train radiomic probability circuit 952 or deep learning probability circuit 957, according to techniques described herein. Training radiomic probability circuit 952 or deep learning probability circuit 957 may include training a machine learning classifier, including an LDA classifier, a CNN, a random forest classifier or a QDA classifier. In one embodiment, training circuit 1051 is configured to access a training dataset of digitized images of a region of interest demonstrating BCa. The training dataset includes images of tissue that responded to NAC, and different images of tissue that did not respond to NAC. Training circuit 1051 may be further configured to access a testing dataset of digitized images of a region of interest demonstrating BCa, where the testing dataset includes images of tissue that responded to NAC, and different images of tissue that did not respond to NAC. In this embodiment, the machine learning classifier or CNN is trained and tested using the training dataset of images and the testing dataset of images. Training the machine learning classifier or the CNN may include training the machine learning classifier or the CNN until a threshold level of accuracy is achieved, until a threshold time has been spent training the machine learning classifier or CNN, until a threshold amount of computational resources have been expended training the machine learning classifier or CNN, or until a user terminates training. Other training termination conditions may be employed.

FIG. 10 further illustrates a personalized medicine system 1060. Apparatus 1000 may be configured to transmit the classification, the final probability, the combined ML probability, the personalized treatment plan, the set of radiomic features, the set of patches, or the diagnostic DCE-MRI image to the personalized medicine device 1060. Personalized medicine device 1060 may be, for example, a CADx system, a BCa NAC response prediction system, or other type of personalized medicine device that may be used to facilitate the classification of tissue or the prediction of response to chemotherapy, including NAC. In one embodiment, personalized treatment plan circuit 1053 may control personalized medicine system 1060 to display the classification, the final probability, the combined ML probability, the personalized treatment plan, the set of radiomic features, the set of patches, or the diagnostic DCE-MRI image on a computer monitor, a smartphone display, a tablet display, or other displays.

Figure 11:
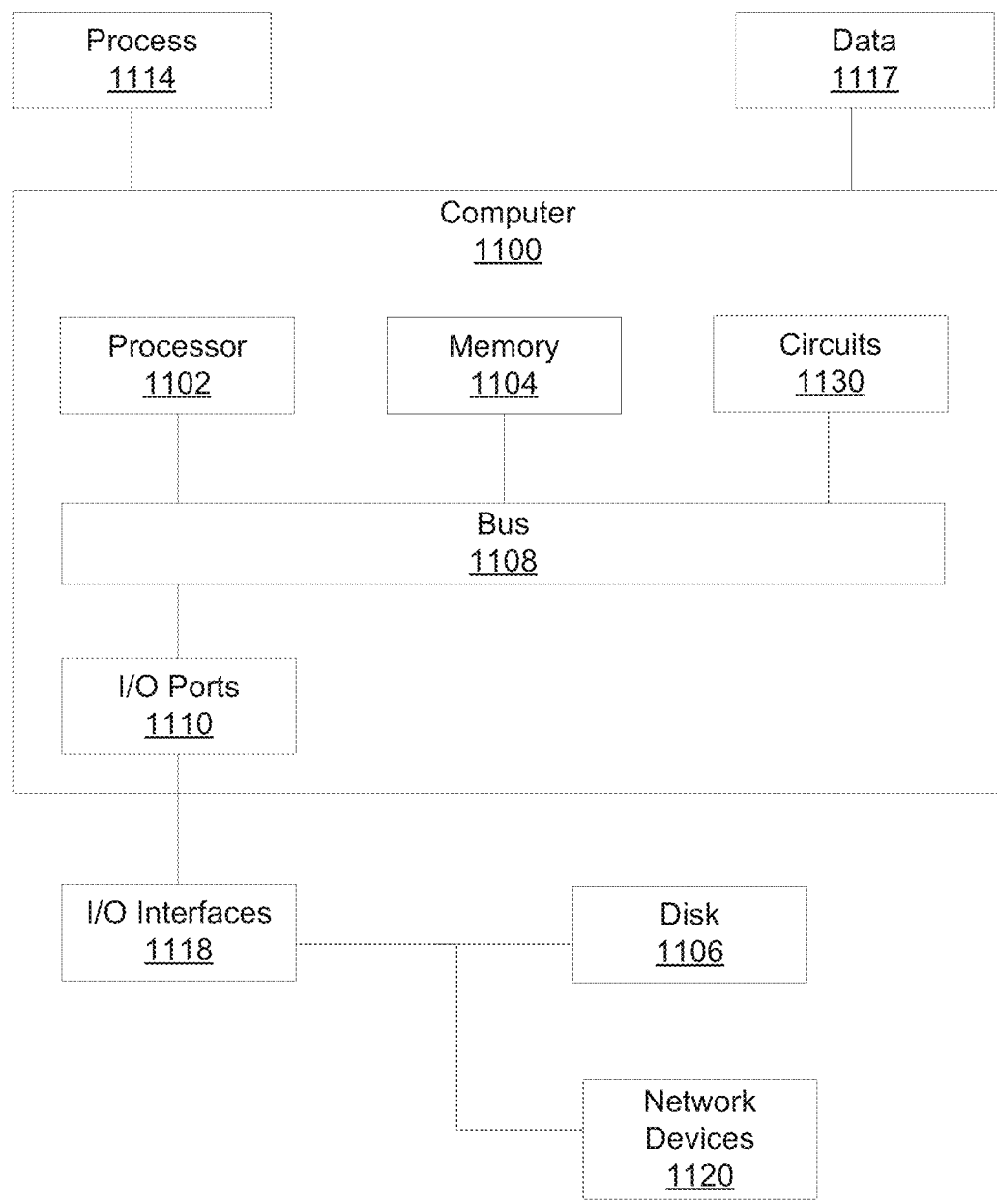
FIG. 11 illustrates an example computer in which embodiments described herein may operate.

FIG. 11 illustrates an example computer 1100 in which example methods illustrated herein can operate and in which example methods, apparatus, circuits, operations, or logics may be implemented. In different examples, computer 1100 may be part of a chemotherapy response prediction system or apparatus, an MRI system, a digital whole slide scanner, may be operably connectable to a chemotherapy response prediction system or apparatus, or an MRI system.

Computer 1100 includes a processor 1102, a memory 1104, and input/output (I/O) ports 1110 operably connected by a bus 1108. In one example, computer 1100 may include a set of logics or circuits 1130 that perform operations for or a method of predicting response to NAC in BCa using a combined ML probability. Thus, the set of circuits 1130, whether implemented in computer 1100 as hardware, firmware, software, and/or a combination thereof may provide means (e.g., hardware, firmware, circuits) for predicting response to NAC in a BCa patient. In different examples, the set of circuits 1130 may be permanently and/or removably attached to computer 1100.

Processor 1102 can be a variety of various processors including dual microprocessor and other multi-processor architectures. Processor 1102 may be configured to perform operations or steps of methods claimed and described herein. Memory 1104 can include volatile memory and/or non-volatile memory. A disk 1106 may be operably connected to computer 1100 via, for example, an input/output interface (e.g., card, device) 1118 and an input/output port 1110. Disk 1106 may include, but is not limited to, devices like a magnetic disk drive, a tape drive, a Zip drive, a flash memory card, or a memory stick. Furthermore, disk 1106 may include optical drives like a CD-ROM or a digital video ROM drive (DVD ROM). Memory 1104 can store processes 1114 or data 1117, for example. Data 1117 may, in one embodiment, include digitized pathology slides. Disk 1106 or memory 1104 can store an operating system that controls and allocates resources of computer 1100.

Bus 1108 can be a single internal bus interconnect architecture or other bus or mesh architectures. While a single bus is illustrated, it is to be appreciated that computer 1100 may communicate with various devices, circuits, logics, and peripherals using other buses that are not illustrated (e.g., PCIE, SATA, Infiniband, 794, USB, Ethernet).

Computer 1100 may interact with input/output devices via I/O interfaces 1118 and input/output ports 1110. Input/output devices can include, but are not limited to, CT systems, MRI systems, digital whole slide scanners, an optical microscope, a keyboard, a microphone, a pointing and selection device, cameras, video cards, displays, disk 1106, network devices 1120, or other devices. Input/output ports 1110 can include but are not limited to, serial ports, parallel ports, or USB ports.

Computer 1100 may operate in a network environment and thus may be connected to network devices 1120 via I/O interfaces 1118 or I/O ports 1110. Through the network devices 1120, computer 1100 may interact with a network. Through the network, computer 1100 may be logically connected to remote computers. The networks with which computer 1100 may interact include, but are not limited to, a local area network (LAN), a wide area network (WAN), or other networks, including the cloud.

Figure 12:
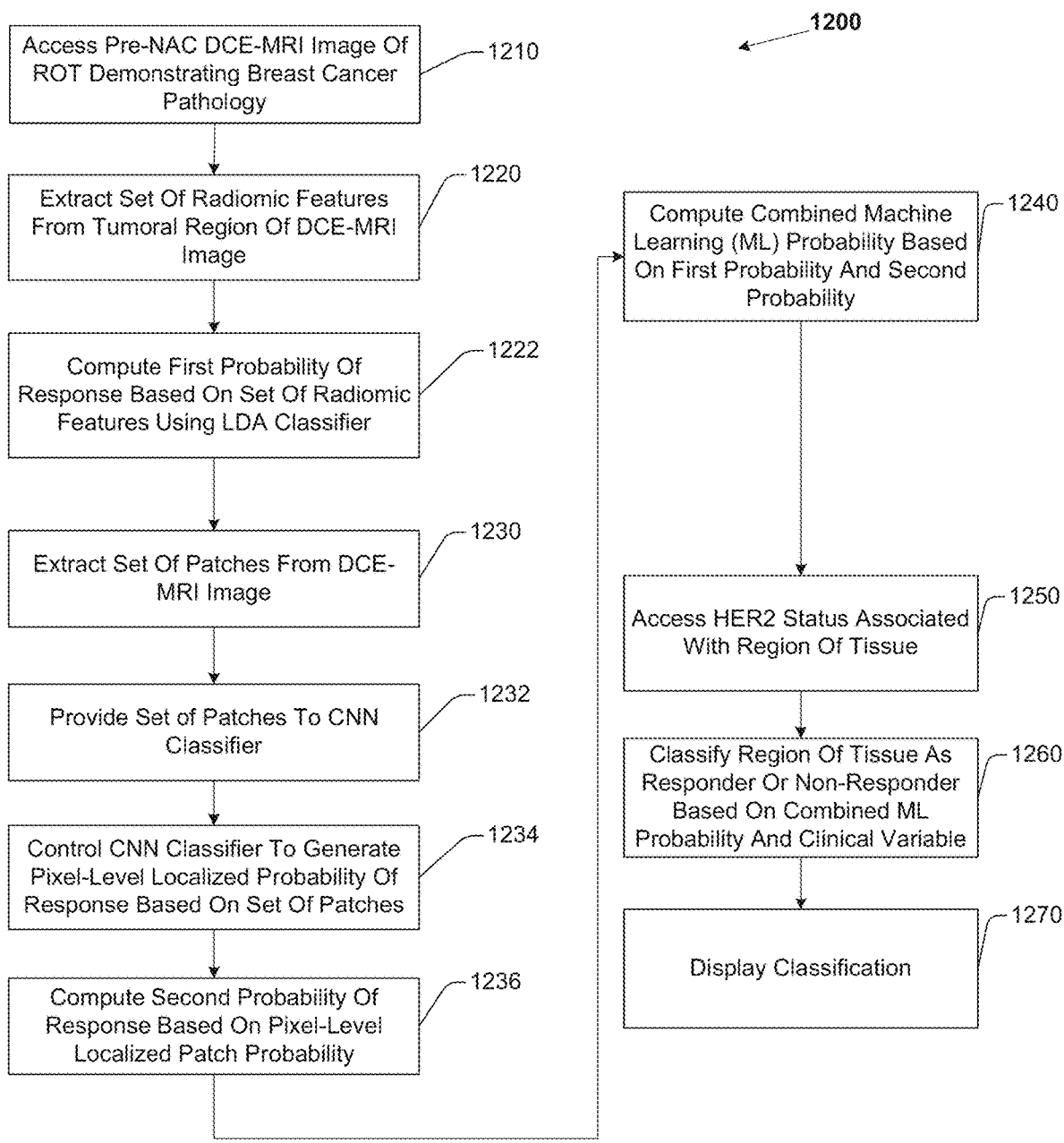
FIG. 12 illustrates an example method for classifying a region of tissue demonstrating BCa as a responder or non-responder.

FIG. 12 illustrates an example method 1200 for classifying a region of tissue as a responder to neo-adjuvant chemotherapy (NAC) or as a non-responder. Method 1200 includes, at 1210 accessing a DCE-MRI image of a region of tissue demonstrating BCa pathology, the region of tissue including a tumoral region. The DCE-MRI image includes a plurality of pixels, a pixel having an intensity. Accessing the DCE-MRI image includes acquiring electronic data, reading from a computer file, receiving a computer file, reading from a computer memory, or other computerized activity not practically performed in the human mind.

Method 1200 also includes, at 1220, extracting a set of radiomic features from the tumoral region represented in the DCE-MRI image. The set of radiomic features includes at least one Laws feature, at least one Haralick feature, and at least one Gabor feature. In one embodiment, the set of radiomic features includes a skewness of a Laws E5E5 feature; a kurtosis of a Haralick entropy feature; a kurtosis of a Laws R5R5 feature; a median of a Laws E5E5 feature; a skewness of a co-occurrence of local anisotropic gradient orientations (CoLIAGe) energy feature; a kurtosis of a Laws W5W5 feature; a kurtosis of a first Gabor feature; and a kurtosis of a second, different Gabor feature. In another embodiment, the set of radiomic features may include other, different radiomic features, other first order statistics computed from the radiomic features, or another, different number of radiomic features. Extracting the set of radiomic features includes acquiring electronic data, reading from a computer file, receiving a computer file, reading from a computer memory, or other computerized activity not practically performed in the human mind.

Method 1200 also includes, at 1222, computing, using a linear discriminant analysis (LDA) classifier trained to distinguish tissue that will respond to NAC from tissue that will not respond to NAC, a first probability that the region of tissue will respond to NAC. The LDA classifier computes the first probability based, at least in part, on the set of radiomic features. Computing the first probability includes acquiring electronic data, reading from a computer file, receiving a computer file, reading from a computer memory, or other computerized activity not practically performed in the human mind.

Method 1200 also includes, at 1230, extracting a set of patches from the tumoral region. In one embodiment, the set of patches includes, for each pixel of the tumoral region respectively, a patch centered around the pixel. In another embodiment, the set of patches includes patches centered around fewer than all the pixels in the tumoral region. In one embodiment, a patch has dimensions of 65 pixels by 65 pixels. In another embodiment, a patch may have other, different dimensions.

Method 1200 also includes, at 1232, providing the set of patches to a CNN trained to distinguish tissue that will respond to NAC from tissue that will not respond to NAC. In one embodiment, the CNN is a six block CNN. In this embodiment, a block has a convolution layer batch normalization and an activation function. In this embodiment, blocks 1-5 utilize a rectified linear unit (ReLU) activation function. The final convolutional block of the CNN employs a softmax function to compute the localized patch probability by constraining it to a value between 0 and 1. In this embodiment, the CNN is trained to improve its predictions by minimizing a multinomial logistic objective loss function, a metric computing the distance between the network's predicted probability of response and a patient's binary response outcome (e.g., 0 for non-pCR, 1 for pCR). In another embodiment, the CNN may have another, different architecture. For example, in another embodiment, the CNN may have a different number of blocks or layers, or may employ other functions.

Method 1200 also includes, at 1234, controlling the CNN to generate a pixel-level localized patch probability that the region of tissue will respond to NAC based, at least in part, on the set of patches. In one embodiment, generating a pixel-level localized patch probability also includes computing a distribution of predictions across analyzed patches based on the pixel-level localized patch probability. Generating the pixel-level localized patch probability or computing the distribution of predictions includes acquiring electronic data, reading from a computer file, receiving a computer file, reading from a computer memory, or other computerized activity not practically performed in the human mind.

Method 1200 also includes, at 1236, computing a second probability of response based on the pixel-level localized patch probability. In one embodiment, computing the second probability of response based, at least in part, on the pixel-level localized patch probability, includes computing the second probability of response using a majority voting scheme. Computing the second probability includes acquiring electronic data, reading from a computer file, receiving a computer file, reading from a computer memory, or other computerized activity not practically performed in the human mind.

Method 1200 also includes, at 1240, generating a combined machine learning (ML) probability of response. In one embodiment, the combined ML probability is computed based on the product of the first probability and the second probability. In another embodiment, the combined ML probability may be computed based on the first probability and the second probability using a different technique.

Method 1200 also includes, at 1250, accessing the HER2 status of the patient of whom the DCE-MRI image was acquired. In another embodiment, method 1200 may also include, at 1250, accessing another, different clinical variable associated with the patient of which the DCE-MRI image was acquired. Accessing the HER2 status or different clinical variable associated with the patient of whom the DCE-MRI image was acquired includes acquiring electronic data, reading from a computer file, receiving a computer file, reading from a computer memory, or other computerized activity not practically performed in the human mind.

Method 1200 also includes, at 1260, generating a classification of the region of tissue as a responder or non-responder. Generating the classification may include generating the classification based, at least in part, on the combined ML probability and the HER2 status. In another embodiment, the classification may be based on the combined ML probability, and at least one of the HER2 status or another, different clinical variable associated with the patient of which the DCE-MRI image was acquired. Generating the classification of the region of tissue may, in one embodiment, further include classifying the patient of whom the DCE-MRI image and the HER2 status are acquired as a responder or non-responder based, at least in part, on the combined ML probability and the HER2 status.

Method 1200 further includes, at 1270, displaying the classification. Method 1200 may also include, at 1270, displaying the DCE-MRI image, the set of radiomic features, the set of patches, the first probability, the second probability, the combined ML probability, or the HER2 status. Displaying the classification includes acquiring electronic data, reading from a computer file, receiving a computer file, reading from a computer memory, or other computerized activity not practically performed in the human mind.

Examples herein can include subject matter such as an apparatus, a NAC response prediction system, a personalized medicine system, a CADx system, a processor, a system, circuitry, a method, means for performing acts, steps, or blocks of the method, at least one machine-readable medium including executable instructions that, when performed by a machine (e.g., a processor with memory, an application-specific integrated circuit (ASIC), a field programmable gate array (FPGA), or the like) cause the machine to perform acts of the method or of an apparatus or system for predicting response to NAC in BCa, according to embodiments and examples described.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage device", as used herein, refers to a device that stores instructions or data. "Computer-readable storage device" does not refer to propagated signals. A computer-readable storage device may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage device may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, and other media from which a computer, a processor or other electronic device can read.

"Circuit", as used herein, includes but is not limited to hardware, firmware, software in execution on a machine, or combinations of each to perform a function(s) or an action(s), or to cause a function or action from another logic, method, or system. A circuit may include a software controlled microprocessor, a discrete logic (e.g., ASIC), an analog circuit, a digital circuit, a programmed logic device, a memory device containing instructions, and other physical devices. A circuit may include one or more gates, combinations of gates, or other circuit components. Where multiple logical circuits are described, it may be possible to incorporate the multiple logical circuits into one physical circuit. Similarly, where a single logical circuit is described, it may be possible to distribute that single logical circuit between multiple physical circuits.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A non-transitory computer-readable storage device storing computer-executable instructions that, in response to execution, cause a processor to perform operations comprising:

accessing a pre-treatment dynamic contrast enhanced magnetic resonance imaging (DCE-MRI) image of a region of tissue demonstrating breast cancer (BCa), where the region of tissue includes a tumoral region, where the pre-treatment DCE-MRI image includes a plurality of pixels, a pixel having an intensity;

extracting a set of radiomic features from the tumoral region represented in the pre-treatment DCE-MRI image;

providing the set of radiomic features to a machine learning classifier configured to distinguish tissue that will respond to chemotherapy from tissue that will not respond to chemotherapy;

receiving, from the machine learning classifier, a first probability of response based on the set of radiomic features;

extracting a set of patches from the tumoral region represented in the pre-treatment DCE-MRI image;

providing the set of patches to a convolutional neural network (CNN) configured to distinguish tissue that will respond to chemotherapy from tissue that will not respond to chemotherapy;

receiving, from the CNN, a pixel-level localized patch probability of response, where the CNN computes the pixel-level localized patch probability based, at least in part, on the set of patches;

computing a distribution of predictions across analyzed patches based on the pixel-level localized patch probability;

computing a second probability of response based on the distribution of predictions;

computing a combined machine learning (ML) probability from the first probability and the second probability;

accessing a clinical variable associated with the region of tissue;

computing a final probability of response based on the combined ML probability and the clinical variable;

generating a classification of the region of tissue as a responder or non-responder based, at least in part, on the final probability of response; and displaying the classification.

2. The non-transitory computer-readable storage device of claim 1, where computing the combined ML probability includes computing the product of the first probability and the second probability.

3. The non-transitory computer-readable storage device of claim 1, where the set of radiomic features includes eight radiomic features.

4. The non-transitory computer-readable storage device of claim 3, where the eight radiomic features includes:

a skewness of a Laws E5E5 feature;
a kurtosis of a Haralick entropy feature;
a kurtosis of a Laws R5R5 feature;

a median of a Laws E5E5 feature;
a skewness of a co-occurrence of local anisotropic gradient orientations (CoLlAGe) energy feature;
a kurtosis of a Laws W5W5 feature;
a kurtosis of a first Gabor feature; and
a kurtosis of a second, different Gabor feature.

5. The non-transitory computer-readable storage device of claim 1, where the machine learning classifier is a linear discriminant analysis (LDA) classifier.

6. The non-transitory computer-readable storage device of claim 1, where the CNN is a six-layer CNN.

7. The non-transitory computer-readable storage device of claim 6, where a layer has a convolution layer having batch normalization and a rectified linear unit (ReLU).

8. The non-transitory computer-readable storage device of claim 6, where the CNN employs a multinomial logistic objective loss function for optimization during training.

9. The non-transitory computer-readable storage device of claim 6, where the CNN employs a softmax function to compute the pixel-level localized patch probability.

10. The non-transitory computer-readable storage device of claim 1, where the clinical variable is an HER2 status associated with the region of tissue.

11. The non-transitory computer-readable storage device of claim 10, where the clinical variable further includes an age of a patient of which the pre-treatment DCE-MRI image is acquired, a diameter of the tumoral region, or a hormone receptor status.

12. The non-transitory computer-readable storage device of claim 1, where accessing the pre-treatment DCE-MRI image includes accessing a set of pre-neo-adjuvant chemotherapy (NAC) DCE-MRI images of the region of tissue, the set of pre-NAC DCE-MRI images including a pre-contrast image and at least one post-contrast image.

13. The non-transitory computer-readable storage device of claim 1, the operations further comprising training the machine learning classifier to distinguish tissue that will respond to NAC from tissue that will not respond to NAC.

14. The non-transitory computer-readable storage device of claim 1, the operations further comprising training the CNN to distinguish tissue that will respond to NAC from tissue that will not respond to NAC.

15. An apparatus for predicting response to neo-adjuvant chemotherapy (NAC) in breast cancer (BCa), comprising:
a processor;
a memory configured to store a digitized image of a dynamic contrast enhanced magnetic resonance imaging (DCE-MRI) image of a region of tissue demonstrating BCa;
an input/output (I/O) interface;
a set of circuits; and
an interface that connects the processor, the memory, the I/O interface, and the set of circuits, the set of circuits comprising:
an image acquisition circuit configured to access the DCE-MRI image of the region of tissue demonstrating BCa, where the region of tissue includes a tumoral region;
a radiomic probability circuit configured to:
extract a set of radiomic features from the tumoral region represented in the digitized image; and
compute a first probability that the region of tissue will experience response based on the set of radiomic features;
a patch extraction circuit configured to:
extract a set of patches from the tumoral region;
a deep learning probability circuit configured to:
compute a pixel-level probability that the region of tissue will experience response post-NAC based, at least in part, on the set of patches; and
compute a second probability the region of tissue will experience response post-NAC based on the pixel-level probability;
a combined machine learning (ML) probability circuit configured to:
compute a combined ML score based on the first probability and the second probability;
a clinical variable circuit configured to:
access a clinical variable associated with the region of tissue;
a classification circuit configured to:
generate a classification of the region of tissue as a responder or non-responder based, at least in part, on the combined ML score and the clinical variable; and
a display circuit configured to display the classification and at least one of combined ML score, the clinical variable, or the DCE-MRI image.

16. The apparatus of claim 15, where the patch extraction circuit is configured to:
for each pixel in the tumoral region, extract a patch centered on each pixel, respectively; or
for a threshold number of pixels in the tumoral region, where the threshold number of pixels is less than number of pixels in the tumoral region, extract a patch centered on each of the threshold number of pixels, respectively, where a member of the threshold number of pixels is selected based on a response predictability level of the pixel.

17. The apparatus of claim 15, where the deep learning probability circuit is configured as a convolutional neural network (CNN), the CNN having six blocks;
where a block has a convolution layer having batch normalization and a rectified linear unit (ReLU);
where the CNN employs a multinomial logistic objective loss function for optimization during training; and
where the CNN computes the pixel-level probability using a softmax function.

18. The apparatus of claim 15, where the clinical variable is an HER2 status of the region of tissue.

19. A method, comprising:
accessing an image of a region of tissue of a patient, the region of tissue demonstrating a cancerous pathology, wherein the image includes a plurality of pixels, a pixel having an intensity;
providing the image to a convolutional neural network (CNN);
controlling the CNN to generate a probability that the region of tissue will respond to chemotherapy based, at least in part, on the image;
extracting a set of radiomic features from the image;
accessing an HER2 status of the patient; and
generating a classification of the region of tissue as a responder or non-responder based, at least in part, on the probability, the set of radiomic features, and the HER2 status.

20. The method of claim 19, further comprising:
generating a personalized treatment plan that sets forth a treatment based on the classification; and
delivering the treatment to the patient.

* * * * *